(12) United States Patent
Ontiki

(10) Patent No.: US 12,004,988 B2
(45) Date of Patent: Jun. 11, 2024

(54) DEVICES FOR AND METHODS OF MEASURING, ENHANCING AND FACILITATING CORRECT SPINAL ALIGNMENT

(71) Applicant: Alii R. Ontiki, Los Angeles, CA (US)

(72) Inventor: Alii R. Ontiki, Los Angeles, CA (US)

( * ) Notice: Subject to any disclaimer, the term of this patent is extended or adjusted under 35 U.S.C. 154(b) by 0 days.

(21) Appl. No.: 16/458,856

(22) Filed: Jul. 1, 2019

(65) Prior Publication Data
US 2019/0321211 A1    Oct. 24, 2019

Related U.S. Application Data

(63) Continuation-in-part of application No. 15/563,610, filed as application No. PCT/US2016/025291 on Apr. 4, 2016, now abandoned.

(60) Provisional application No. 62/143,010, filed on Apr. 3, 2015.

(51) Int. Cl.
*A61F 5/00* (2006.01)
*A61B 5/00* (2006.01)
*A61F 5/02* (2006.01)

(52) U.S. Cl.
CPC ............ *A61F 5/026* (2013.01); *A61B 5/4561* (2013.01)

(58) Field of Classification Search
CPC .. A61F 5/02; A61F 5/022; A61F 5/024; A61F 5/026; A61F 5/028; A61F 5/03; A61F 5/0553; A41D 13/05; A41D 13/0525; A41D 13/0531; A61B 5/4561; A61B 5/4566
USPC ........... 128/96.1, 100.1; 602/19, 5, 6, 62, 63
See application file for complete search history.

(56) References Cited

U.S. PATENT DOCUMENTS

| 954,005 A | 4/1910 | Roth | |
|---|---|---|---|
| 2,871,850 A * | 2/1959 | Peckham | A61F 5/028 602/19 |
| 3,346,257 A * | 10/1967 | Whitney | A63B 69/0059 473/215 |

(Continued)

FOREIGN PATENT DOCUMENTS

| DE | 20204936 U1 | 9/2002 |
|---|---|---|
| WO | 2014177673 A1 | 11/2014 |
| WO | 2016161458 A9 | 10/2016 |

OTHER PUBLICATIONS

Notification of Transmittal of the International Search Report, the International Search Report, and the Written Opinion of the International Searching Authority, PCT/US16/25941, dated Jul. 12, 2016.

*Primary Examiner* — Adam Baker

(57) ABSTRACT

Devices for and methods of measuring, enhancing, and facilitating optimal spinal alignment utilizing an Atlas bar with an Atlas pad inserted into an Atlas sheath, configured when worn by a user to rest on three distinct areas of the user's spine: (a) the Atlas pad at the center of the Atlas vertebra; (b) the Atlas sheath at the center of the thoracic region; and (c) a sacrum pad on the Atlas sheath at the center of the sacrum. Atlas pads may be removed and replaced as the user's spinal alignment improves. Devices may be held in place on the user's body with a torso harness, affixed in jackets or other wearable garments, or backpacks. In use, the Atlas bar and sheath are in simultaneous physical contact with three areas of the user's spine, providing tactile feedback to the user and creating proprioceptive awareness resulting in improving spinal alignment over time.

21 Claims, 18 Drawing Sheets

(56) References Cited

U.S. PATENT DOCUMENTS

| | | | |
|---|---|---|---|
| 3,945,376 | A | 3/1976 | Kuehnegger |
| 4,383,523 | A | 5/1983 | Schurman |
| 4,785,803 | A * | 11/1988 | Benckhuijsen ......... A61F 5/026 2/45 |
| 4,951,655 | A | 8/1990 | MacMillan |
| 5,086,757 | A * | 2/1992 | Lestini ................... A61F 5/055 602/17 |
| 5,199,940 | A * | 4/1993 | Morris .................... A61F 5/055 128/845 |
| 5,411,038 | A | 5/1995 | Mollendorf |
| 5,435,563 | A * | 7/1995 | Salvatore ........... A63B 69/0059 128/870 |
| 5,797,955 | A * | 8/1998 | Walters ................... A61F 5/024 602/19 |
| 5,840,051 | A | 11/1998 | Towsley |
| 5,868,691 | A | 2/1999 | Vishnevsky |
| 5,876,361 | A | 3/1999 | Harris |
| 6,312,366 | B1 | 11/2001 | Prusick |
| 6,461,256 | B1 * | 10/2002 | Popeck ............. A63B 69/0059 473/450 |
| 6,626,494 | B2 | 9/2003 | Yoo |
| 6,719,640 | B1 | 4/2004 | Madole |
| 7,086,958 | B2 | 8/2006 | Eigiro |
| 7,322,977 | B2 | 1/2008 | Pettibon |
| 7,967,767 | B2 | 6/2011 | Ogilvie |
| D668,993 | S | 10/2012 | Bin |
| 8,708,834 | B1 * | 4/2014 | Domangue ........ A63B 69/3608 473/207 |
| 8,715,212 | B1 * | 5/2014 | Ely ........................... A61F 5/02 602/18 |
| 10,045,875 | B2 | 8/2018 | Haque |
| 2002/0033626 | A1 | 3/2002 | Yoo |
| 2003/0195445 | A1 * | 10/2003 | Behan .................. A61F 5/0102 602/19 |
| 2005/0203453 | A1 * | 9/2005 | Willner ................... A61F 5/024 602/19 |
| 2005/0245854 | A1 * | 11/2005 | Leuthardt ............... A61F 5/026 602/18 |
| 2006/0238006 | A1 * | 10/2006 | Baranov .................. A47C 7/38 297/284.3 |
| 2008/0228121 | A1 | 9/2008 | Hughes |
| 2010/0204629 | A1 | 8/2010 | Specht |
| 2013/0069411 | A1 * | 3/2013 | Walker .................... A47C 7/38 297/391 |
| 2013/0184615 | A1 | 7/2013 | Johnson |
| 2013/0253393 | A1 * | 9/2013 | Schilling ............... A61F 5/0102 602/5 |
| 2015/0080994 | A1 | 3/2015 | Ho |
| 2015/0202072 | A1 * | 7/2015 | Glazener .................. A61F 5/02 602/18 |
| 2017/0216077 | A1 * | 8/2017 | Chahrour ................ A61F 5/026 |

* cited by examiner

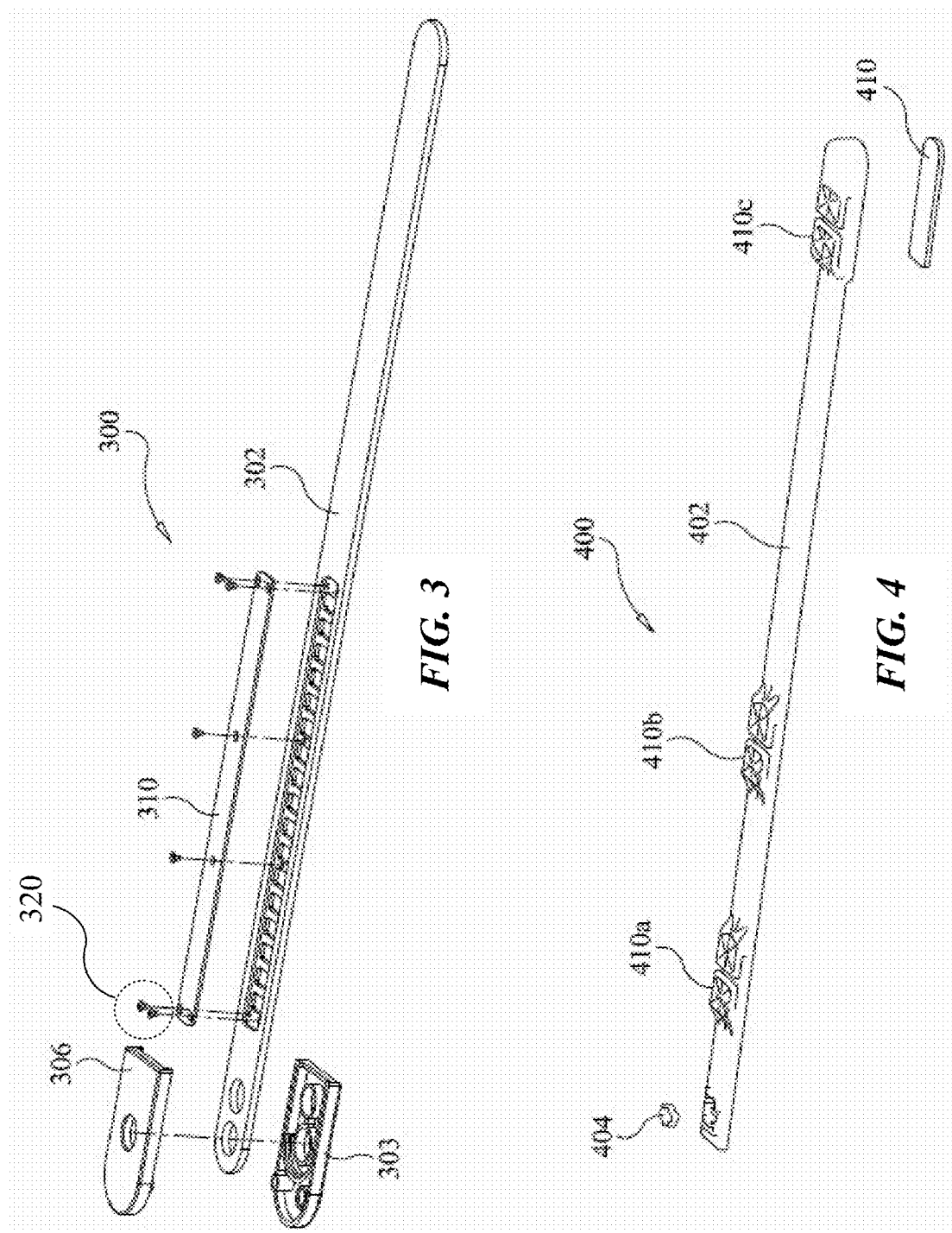

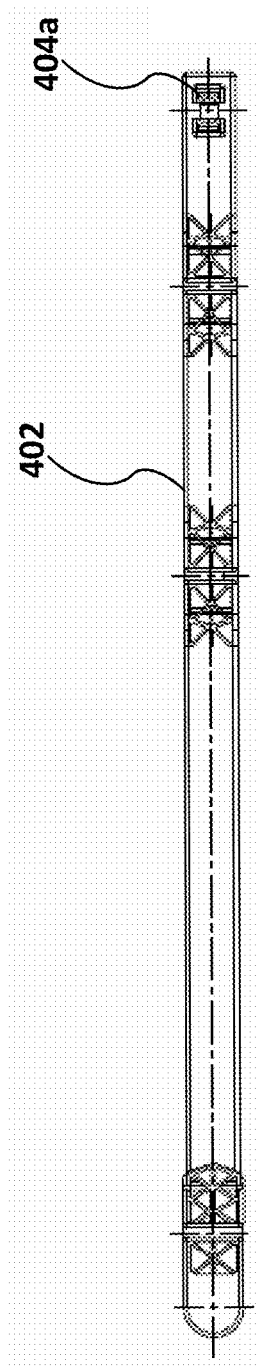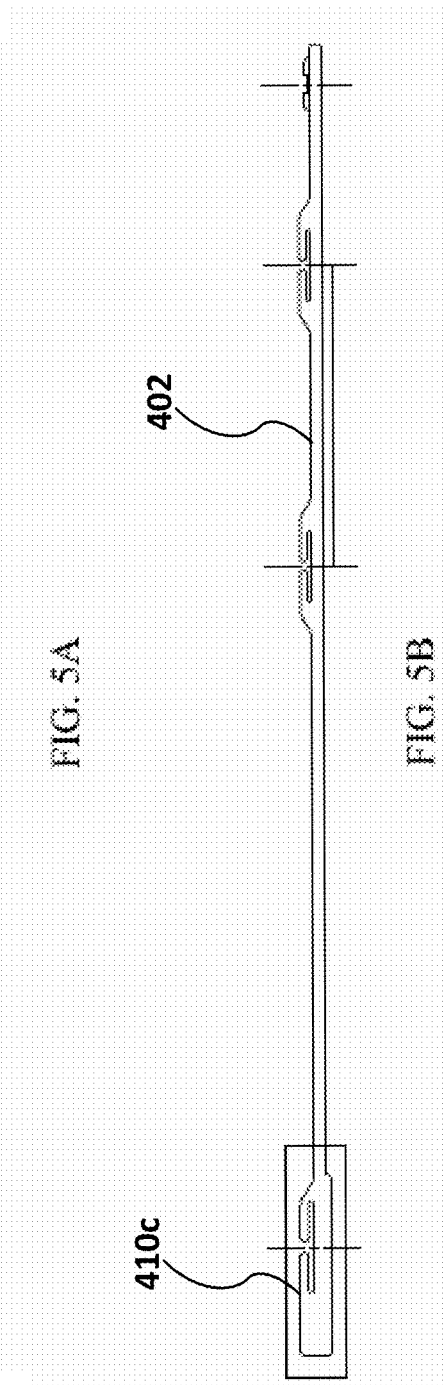
FIG. 5A
FIG. 5B

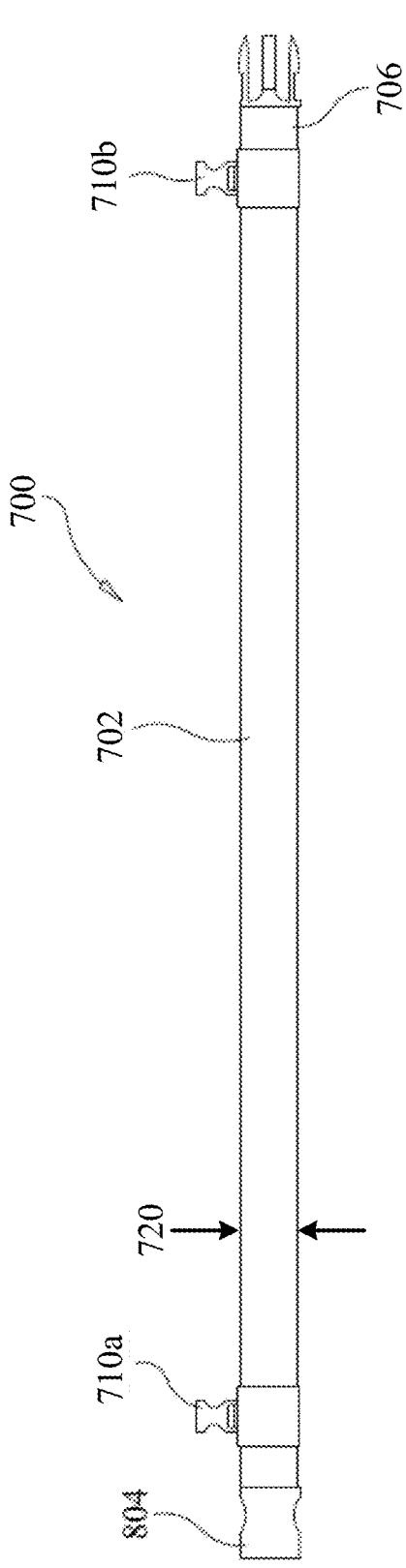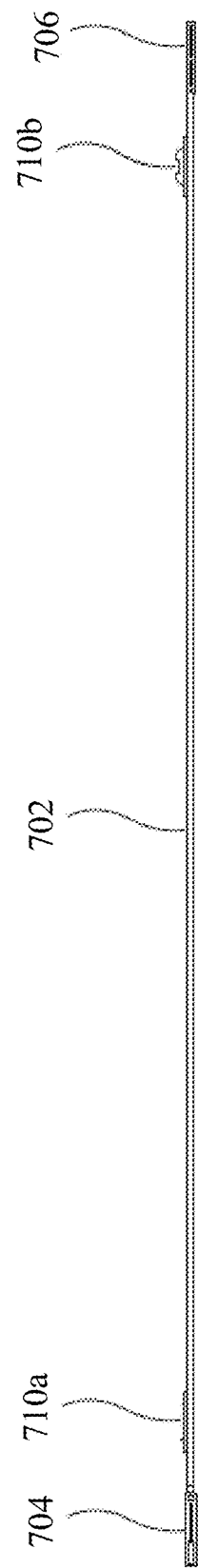
FIG. 7a
FIG. 7b

DEVICES FOR AND METHODS OF MEASURING, ENHANCING AND FACILITATING CORRECT SPINAL ALIGNMENT

CROSS-REFERENCE TO RELATED APPLICATIONS

This application is a continuation-in-part of and claims the priority of U.S. ("U.S.") patent application Ser. No. 15/563,610, entitled "Device and Method for Enhancing and Facilitating Correct Spinal Alignment," filed on Oct. 1, 2017, to inventors Wayne Daniels, Alii R. Ontiki, and George W. Cranford IV, which application is a national stage entry of U.S. Patent Application Serial Number PCT/US2016/025921, entitled "Device and Method for Enhancing and Facilitating Correct Spinal Alignment," filed on Apr. 4, 2016, to inventors Wayne Daniels, Alii R. Ontiki, and George W. Cranford IV, which application claims the priority to U.S. Provisional Patent Application Ser. No. 62/143,010, entitled "Device and Method for Enhancing and Facilitating Correct Spinal Alignment," filed on Jun. 3, 2015, to inventors Wayne Daniels, Alii R. Ontiki, and George W. Cranford IV, the disclosures of which are incorporated by reference herein in their entireties.

BACKGROUND OF THE INVENTION

1. Field of the Invention

The invention relates generally to devices and methods that enhance a person's health and well-being, and more particularly, to devices and methods that operate to measure, improve and properly maintain a person's optimal spinal alignment.

2. Description of the Related Art

Today, many individuals have poor posture which may adversely affect their physical and mental health. For example, poor posture is generally unattractive. Many people perceive individuals with upright posture as interested and alert, while individuals who slouch or stoop may be viewed as lazy, awkward, or frail. These perceptions influence whether others positively or negatively view a person's work or mental condition. In addition to being socially undesirable, poor posture can cause various health problems. With continual poor posture, these health problems can include curvature of the spine and a chronic stooping condition.

Poor posture may result from certain muscles tightening up or shortening while others lengthen and become weak, which often occurs as a result of one's daily activities. The different factors that can impact a person's posture include occupational activities as well as biomechanical factors such as force and repetition. In modern times, frequent use of smartphones, tablets, and personal computers is problematic concerning posture because a person using such digital devices, either at work or for personal pleasure, may sit at their device without proper spinal alignment for extended periods of time, that is, slouched and hunched over, peering at a handheld device or a computer monitor, perhaps while sitting cross-legged or with legs curled under seats, thus creating an epidemic that may be referred to as "Text Neck" or "Tech Neck."

Strictly speaking, "text neck" refers to a repeated stress injury and pain resulting from excessive watching or texting on handheld mobile devices for long periods of time, where a user looks downward into a mobile screen with a forward head posture and rounding of the shoulders and forces on the neck increase as the user's head tilts forward. Text neck may lead to harmful conditions such as neck pain and neck spasms, upper back pain, shoulder pain, chronic headaches, and increased curvature of the spine. Text neck may also sometimes be referred to as "tech neck," which is similar but also encompasses working on a laptop or desktop at home or in an office for extended periods of time with poor posture, resulting in the same harmful symptoms that are found in text neck. These are problems that are found in all age groups but particularly in the young adult population and are only going to become more widespread.

Other sources of poor spinal alignment may be repetitive motion without frequent breaks and also sitting with poor posture for long periods without interruption. If one spends a substantial part of one's day in a certain position without frequent reprieves, the spine tends to orient itself to that position. For example, if someone is constantly leaning over to pick up objects, gradually the spine will start to develop a more exaggerated forward curve of the thoracic spine. In other words, poor spinal alignment may be caused either by prolonged periods of repeated motions, or by remaining fixed in one particular position for prolonged periods.

From the foregoing it is evident that poor spinal alignment is at present a common affliction suffered by more and more people and thus there is a need for spinal measuring and alignment devices and methods of using these devices that will enable a person to measure and then improve his or her spinal alignment. The typical remedies for the so-called "text neck" include performing exercises and stretches to improve posture, in the case of texting bringing the handheld device to eye level, or in the case of personal computers to sit in a chair that reclines and provides better lumbar support. Also, there are devices designed to provide traction to a user's spine or to exercise back and shoulder muscles as well as belts and straps to promote proper spinal alignment.

None of these remedies or devices measure the degree of a user's spinal misalignment nor do they provide constant feedback from a device that can used by a user for extended periods of time and that is readily adjustable as the user's spinal alignment improves. Thus, there is a need for improved measuring and spinal alignment enhancement devices that may be worn by the user either for short or extended periods of time, while undertaking various stationary or non-stationary positions or activities throughout the day, and that should be lightweight, comfortable and adjustable to the user's changing spinal alignment.

SUMMARY

Devices for and methods of measuring, correcting, improving, and properly maintaining a person's posture and spinal alignment are disclosed. An adjustable measuring and spinal alignment device in accordance with the invention may include a flat or rounded metal, fabric, wood, or plastic Atlas bar and an Atlas sheath into which the Atlas bar can be removably inserted so that the length of the Atlas bar can be correspondingly adjusted to the length of the user's spine.

The Atlas bar may include a removable, adjustable Atlas pad affixed to a top end of the Atlas bar, where the Atlas pad is configured to rest below the base of the skull, i.e., at the first vertebra (C1) of the cervical region of the spine (or Atlas vertebra), of a user. Being removable and adjustable, Atlas pads of varying dimensions and shapes may be used as required to accommodate a user's particular need, e.g., replacing an Atlas pad with a smaller-in-length Atlas pad as the user's spinal alignment improves. Additionally, the length of an Atlas bar together with its Atlas sheath may be adjusted relative to the length of the spine of a particular user. That is, a sacrum pad positioned on the bottom end of the Atlas sheath that holds an Atlas bar should rest upon the lower spine of the user in alignment of the center of the sacrum (as explained in more detail below) and remain firmly in contact with the user's sacrum with a sacrum belt throughout his usage of the adjustable measuring and spinal alignment device.

With the position of the sacrum pad aligned with the center of the sacrum of a user as a starting point, the next step is to determine the position of the Atlas pad on the Atlas bar, by adjusting the Atlas bar within its Atlas sheath so that the Atlas pad is resting at the Atlas vertebra of the user while the sacrum pad remains positioned on the sacrum of the user. With the position of the Atlas pad on the Atlas bar determined, the user may now select the Atlas Pad to be placed on the Atlas Bar, specifically its length, shape, and material. Between the position of the Atlas pad and the sacrum pad on the Atlas sheath, there is a third contact area where the Atlas sheath holding the Atlas bar is in contact with and centered on the thoracic region of the user's spine (as explained in more detail below).

Once the Atlas bar is configured, the Atlas bar and Atlas sheath may be worn on the body of a user and held in place by a torso harness comprising a left-shoulder suspender and a right-shoulder suspender (or shoulder straps), that are placed over the torso of a user with an Atlas bar and its Atlas sheath attached to the torso harness and held in place and centered on the thoracic region of the spine of the user. The torso harness may also include a connecting strap connecting the two suspenders, a thoracic belt, and a sacrum belt. Instead of a torso harness, the means that holds an Atlas bar and Atlas sheath against the spine of the user may take the form of a vest or corset comprised of lightweight nylon, cotton, polyester or other like materials and worn on the body in the form of clothing, e.g., a jacket or sweatshirt, with the clothing having a channel or tubing sewn or heat fused therein allowing removable insertion of an Atlas sheath. In other embodiments, the webbing or the like may be attached by way of brackets or buckles to backpacks, office desks, car seats, etc., or other stationary objects.

In use, the adjustable measuring and spinal alignment device of the present disclosure encourages simultaneous physical contact of an Atlas pad on an Atlas bar and an Atlas sheath into which the Atlas bar is adjustably inserted with three specific regions or areas of the user's spine: (a) the Atlas pad at the neck region of the spine known as cervical spine consisting of seven vertebrae, specifically the Atlas vertebra; (b) the Atlas sheath at the center of the thoracic region of the spine located below the cervical spine and consisting of twelve vertebrae; and (c) a sacrum pad at the bottom of the Atlas sheath centered on the sacrum of the spine consisting of five vertebrae, which is located below the lumbar region of the spine (consisting of five vertebrae) that is located below the thoracic region.

When used in various settings, the adjustable measuring and spinal alignment device facilitates correct spinal posture by creating proprioceptive awareness and recruitment of suboccipital muscles and increasing spinal tension and adaptability in movement. That is, the physical contact points on the user's spine of the adjustable measuring and spinal alignment device provides stimulation of nerve endings in muscles and joints that gives the user a sense of body position and self-movement. In other words, it's as if there's someone constantly telling the user to stand or sit up straight.

Over time, the user will develop awareness of his improper posture and adjust his posture to acquire new and correct postural habits. As the user's spinal posture improves, the Atlas pad used on the Atlas bar of the adjustable measuring and spinal alignment device may be removed and replaced with an Atlas pad of different dimensions and shapes, most importantly the length of the Atlas pad may be decreased. For example, the distance between the center of the arc where the Atlas pad rests on the Atlas vertebra and the Atlas bar itself may be decreased as the posture improves, as the misalignment of the spine is reduced.

The adjustable measuring and spinal alignment device is intended for use in all types of settings and for either short or extended periods of time. For example, the adjustable measuring and spinal alignment device may be worn for as little as one half hour to one hour daily to get results in a very short time frame, e.g., three months. It can be worn in most settings such as standing, sitting, walking, working out, or training most athletic endeavors. For example, the measuring and spinal alignment device may be used while working in an office or at a computer for several hours, working in an occupation that requires physical movement and labor, or while exercising or participating in specific sporting or recreational activities.

Methods of using an embodiment comprising the adjustable measuring and spinal alignment device are also disclosed. It is crucial that the Atlas pad and the sacrum pad of the Atlas sheath are positioned correctly on the user's spine. The first step in using the adjustable posture apparatus is to adjust the adjustable measuring and spinal alignment device to its proper length for a particular user. This is accomplished by holding the sacrum pad on the bottom of the Atlas sheath of the adjustable measuring and spinal alignment device at the center of the sacrum of the user and adjusting the adjustable measuring and spinal alignment device by pulling the Atlas bar (inserted into the Atlas sheath) with an Atlas pad at the top up from the sheath until the Atlas pad is touching the back of the user's neck at the center of his Atlas vertebra.

Thus, the adjustable measuring and spinal alignment device (i.e., the Atlas bar and the Atlas sheath) must first be configured to its proper length for a particular user, where the proper height is determined by the distance between the Atlas pad on the Atlas bar and the sacrum pad on the Atlas sheath of the Atlas bar. With two contact points on the spine being the Atlas vertebra and the center of the sacrum, the third contact point is the thoracic spine of the user, specifically, the center of the thoracic portion of the spine consisting of twelve vertebrae. When the Atlas bar and the Atlas sheath are placed on the user's torso, for example, with a torso harness, and the Atlas pad and the sacrum pad are properly positioned on the for the spine of that particular user, the Atlas sheath itself will naturally come in contact with the center vertebrae of the thoracic region of the user's spine.

A method of using an example embodiment comprising the adjustable measuring and spinal alignment device is disclosed whereby an adjustable measuring and spinal alignment device in accordance with the invention is attached to a torso harness that is then fitted onto a user. First, adjust the circumference of a sacrum belt, which may be designed with rubber inlays stitched to the inside of the sacrum belt for improved adhesion and stability, to secure a sacrum pad to the center of the sacrum of the user. It is crucial that the sacrum pad and the Atlas pad are positioned correctly on the Atlas sheath and the Atlas bar, respectively. Accordingly, the sacrum pad is the starting point: adjust the sacrum belt to hold the sacrum pad at the center of the user's sacrum and then make other adjustments to the adjustable measuring and spinal alignment device so that the Atlas pad is positioned at the Atlas vertebra of the user. The position of the sacrum belt should be around the thickest part of the user's gluteal muscles about even with the greater trochanters of the user's femurs on the side of the user's pelvis. This is a few inches below where a user would normally wear a waist belt. If the user sits down on a hard chair, the bottom of the adjustable posture device should barely touch or almost touch the seat of the chair.

Next, the user should tighten the sacrum belt securely, making sure the sacrum pad is still in its correct position. Then the user puts the right and left suspenders of the torso webbing over his shoulders such that torso webbing is not too loose or too tight. If too tight, this may result in the sacrum belt being pulled up from its proper position that will drastically inhibit the effectiveness of the adjustable measuring and spinal alignment device; if too loose, the suspenders may fall off the shoulders of the user. To help ensure that the suspenders don't fall off the shoulders, the position of the connection of the suspenders relative to the sacrum belt should be within approximately one inch of the sacrum side release belt buckle when fastened.

Once the torso harness is adjusted and the Atlas bar and Atlas sheath are firmly in place on the user's spine, there should be three contact points of the Atlas bar and the Atlas sheath on the user's spine. The first is the Atlas pad at the center of the Atlas vertebra of the user, the second is the Atlas sheath in contact with the center of the thoracic region of the user's spine, and the third is a sacrum pad of the Atlas sheath positioned at the center of the sacrum of the user. In the final step, a user may stand sideways in front of a mirror and check to make sure the Atlas pad and the sacrum pad are positioned correctly at the top and bottom of the spine, respectively. To repeat, it is crucial that the sacrum belt be worn so that the sacrum pad is even with the lower part of the user's sacrum and that the sacrum belt should wrap around the greater trochanters of the femurs of the user and be even with his pubic symphysis.

Once the torso harness is in place, the user may use it in everyday activities, such as stationary activities, e.g., sitting at a desk, or non-stationary activities, such as playing golf or exercising, where the activities may be for an hour or less or for several hours.

The separate Atlas bar and Atlas sheath, once configured for a particular user's spine, may be manually applied by a third-party spotter, trainer, physical therapist, or the like, rather than placed on a user's torso with a torso harness. For example, a removable handle or grip may be attached to the Atlas sheath, which can then be used by a professional facilitator to initially measure the user's spinal misalignment, by a spotter, trainer or physical therapist guiding a user's spinal alignment in performing various calisthenics or weight lifting exercises, by a physical therapist, chiropractor or physical medicine and rehabilitation (PM&R) doctor assisting a patient with the proper positioning of his or her spine when undergoing physical therapy or rehabilitation, etc.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The examples of the invention described below can be better understood with reference to the following figures. The components in the figures are not necessarily to scale, emphasis instead being placed upon illustrating the principles of the invention. In the figures, like reference numerals designate corresponding parts throughout the different views.

FIG. 3 shows a rear perspective view of another example of an Atlas bar that may be used with the assembled adjustable measuring and spinal alignment apparatus of FIG. 1, with an exploded perspective view of an adjustable Atlas pad assembly having a top face and a bottom face.

FIG. 4 shows a rear perspective view of an example of an Atlas sheath that may be used with the Atlas bar of the assembled adjustable measuring and spinal alignment apparatus of FIG. 1.

FIG. 5a shows a rear elevation view of the example of an Atlas sheath shown in FIG. 4.

FIG. 5b shows a side elevation view of the example of an Atlas sheath shown in FIG. 4.

FIG. 6b shows a top plan view of the adjustable measuring and spinal alignment device shown in FIG. 6a.

FIG. 6c shows a side elevation view of the adjustable measuring and spinal alignment device shown in FIG. 6a.

FIG. 7a shows a rear elevation view of an example implementation of a sacrum belt in accordance with the invention that is unconnected.

FIG. 7b shows a top plan view of the sacrum belt shown in FIG. 7a.

FIG. 15b shows a rear elevation view of the strap slide shown in FIG. 15a.

FIG. 15c shows a side elevation view of the strap slide shown in FIG. 15a.

DETAILED DESCRIPTION

In the following description of the preferred and various alternative embodiments, reference is made to the accompanying drawings that form a part hereof, and in which is shown by way of illustration a specific embodiment in which the invention may be practiced. It is to be understood that other embodiments may be utilized, and various structural changes may be made without departing from the spirit and scope of this invention.

Figure 1:
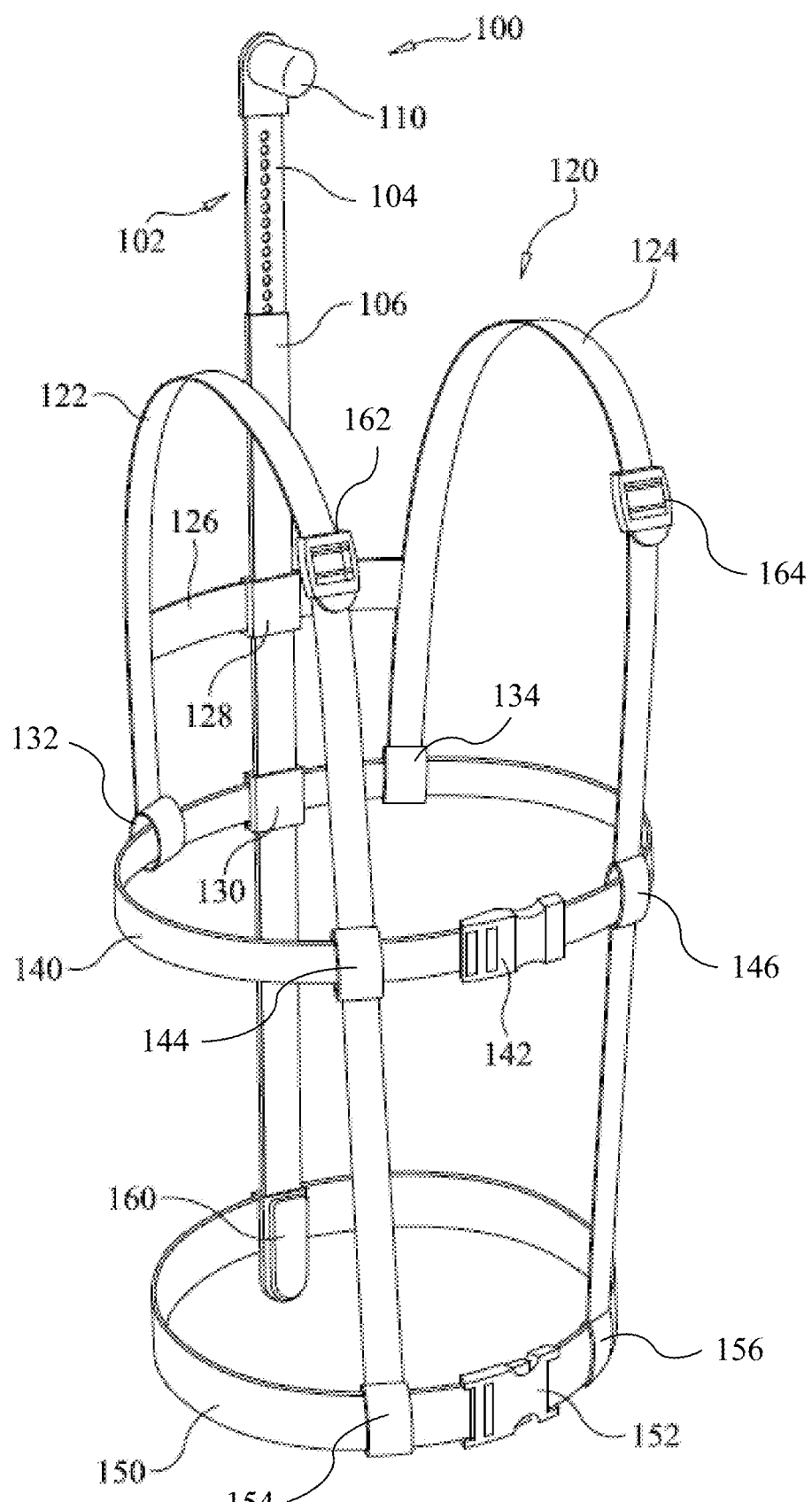
FIG. 1 shows a front perspective view of an example implementation of an assembled adjustable measuring and spinal alignment apparatus in accordance with the invention, comprising an Atlas bar with an Atlas pad inserted into an Atlas sheath with a sacrum pad and a torso harness configured to hold the Atlas bar and the Atlas sheath against the spine of the user.

FIG. 1 shows a front perspective view of an example implementation of an assembled adjustable measuring and spinal alignment apparatus 100 in accordance with the invention. In FIG. 1, an adjustable measuring and spinal alignment device 102 is shown, where the adjustable measuring and spinal alignment device 102 comprises an Atlas bar 104 and an Atlas sheath 106 that is configured to adjustably receive and hold the Atlas bar 104.

Also shown in FIG. 1 is a torso harness 120 comprising webbing in the form of a right-shoulder suspender 122, a left-shoulder suspender 124, a thoracic belt 140, and a sacrum belt 150, which torso harness 120 is designed to hold the assembled adjustable measuring and spinal alignment apparatus 100 in place on the torso of a user. The right-shoulder suspender 122 and the left-shoulder suspender 124 may be connected by connecting strap 126. The connecting strap 126 and the thoracic belt 140 may each be threaded through movable strap slides 128 and 130, respectively, with each strap slide containing a vertical slot configured to receive and hold in place the sheath 106 and a horizontal slot configured to receive and hold webbing of the torso harness 120 in a desired position. There is a strap slide (not shown) that connects the bottom of the sheath 106 to the sacrum belt 150.

One end of the right-shoulder suspender 122 and the left-shoulder suspender 124 may be connected to the rear of the thoracic belt 140 by sewing one end of right-shoulder suspender 122 and left-shoulder suspender 124 to webbing loops 132 and 134, respectively, and the right-shoulder suspender 122 and the left-shoulder suspender 124 may also be connected to the front of the thoracic belt 140 by sewing right-shoulder suspender 122 and left-shoulder suspender 124 onto webbing loops 144 and 146, respectively, such that the right-shoulder suspender 122 and the left-shoulder suspender 124 can be snugly fitted over the right-shoulder and the left-shoulder, respectively, of a user. Each of the right-shoulder suspender 122 and the left-shoulder suspender 124 may include inserted therein adjustable strap buckles 162 and 166 that are used to adjust the two shoulder suspenders.

The other end of the right-shoulder suspender 122 and the left-shoulder suspender 124 may then be connected to the front of the sacrum belt 150 by sewing the other end of right-shoulder suspender 122 and left-shoulder suspender 124 to webbing loops 154 and 156, respectively, such that the Atlas pad 110 and the sacrum pad 160 are properly positioned at the center of the Atlas vertebra and the center of the sacrum of a user as explained in more detail below. Webbing loops 132, 134, 144, 146, 154, and 156 are loops made of the same material as the straps and belts of the torso harness and are configured over to fit snugly over the corresponding strap or belt. In lieu of webbing loops, the right-shoulder suspender 122 and the left-shoulder suspender may be connected to the thoracic or the sacrum belts by cam, spring, or side release buckles of varying sizes.

The thoracic belt 140 may include a side release buckle 142 and the sacrum belt 150 may include a side release buckle 152, which buckles allow a user to quickly and easily fasten and unfasten the respective belts. Sacrum pad 160 is fastened at the bottom end of the Atlas sheath 106 and rests upon the center of the sacrum of the user when the adjustable measuring and spinal alignment apparatus 100 is placed around the torso of the user.

Figure 2:
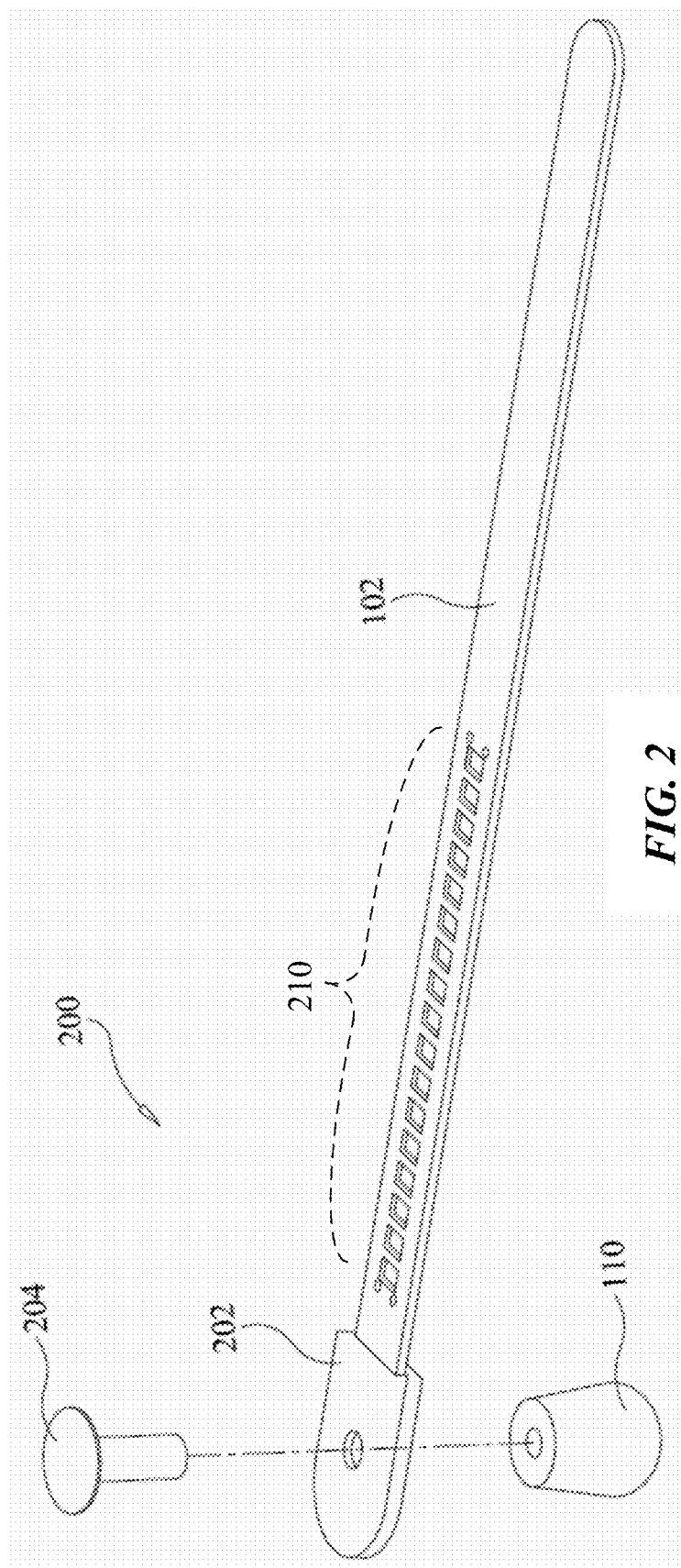
FIG. 2 shows a rear perspective view of an example of the Atlas bar of the assembled adjustable measuring and spinal alignment apparatus of FIG. 1, together with an exploded perspective view of an adjustable Atlas pad.

Turning to FIG. 2, a side perspective view 200 of the Atlas bar 102 of FIG. 1 is shown. At the top of the Atlas bar 102 there may be placed an Atlas pad assembly 202, through which an Atlas pad threaded pin 204 may be inserted to connect with an Atlas pad 110 thus allowing easy and quick removal and replacement of the Atlas pad 110 if desired. Also shown is a row of a plurality of indents 210 that are utilized to hold the Atlas bar 102 in a desired position with a plastic locking key.

Turning to FIG. 3, a side perspective view 300 of another example implementation of an Atlas bar 302 is shown, which Atlas bar 302 includes pad assembly top face 304 and Atlas pad assembly bottom face 306, which Atlas pad assembly top face 304 and Atlas pad assembly bottom face 306 when joined, form an Atlas pad assembly that may be placed at the top of the Atlas bar 302 and through which an Atlas pad pin 204 (FIG. 2) may be inserted to connect with an Atlas pad 110 (FIG. 2) thus allowing easy and quick removal and replacement of the Atlas pad 110 (FIG. 2).

The Atlas bar 302 may also include Atlas bar magnetic strip 310 that may be positioned into a recess formed in the Atlas bar 302 and held in place with a plurality of screws 320. When Atlas bar 302 (FIG. 1) is inserted into an Atlas sheath 106, Atlas bar magnetic strip 310 assists in adjusting and holding the sheath with a magnetic locking key (not shown) on the top of the sheath 106 in place by providing a magnetic field. A possible benefit of the Atlas bar magnetic strip 310 is improved blood flow through the spine of the user, as magnetic bracelets are known to provide localized improved blood flow dependent on the strength of the magnetic field of the device.

FIG. 4 shows a rear perspective view 400 of an Atlas sheath 402 configured to receive and hold the Atlas bar 104 of FIG. 1. Atlas sheath 402 may include a locking key assembly that is configured to hold the Atlas bar in place with a sheath locking key 404 when an Atlas bar has been properly inserted and adjusted in the Atlas sheath 402. The locking key assembly may also include a magnet (not shown) that may be placed into the sheath locking key 404, such that it will attach to the magnetic strip 310, FIG. 3, of the Atlas bar 104 and hold it in its desired position in the Atlas sheath 402.

Sacrum pad 410 may be placed on the inside of the Atlas sheath 402 at its bottom so as to rest on the center of the sacrum of the user when an Atlas bar and Atlas sheath are worn by the user. The Atlas sheath 402 may also include strap slides 410a, 410b, and 410c that are positioned so as to have connecting strap 126 (FIG. 1), a thoracic belt 140 (FIG. 1), and sacrum belt 150 (FIG. 1), respectively, horizontally pass through horizontal slots of the strap slides 410a, 410b, and 410c.

The Atlas sheath 402 may be made of plastic and in contrast to movable strap slides 128 and 130 of FIG. 1, strap slides 410a, 410b, and 410c of Atlas sheath 402 are built in when forming the Atlas sheath 402. Strap slides 410a, 410b, and 410c in general may have a horizontal slot having a width of approximately 2.0 inches that allows connecting strap 126, thoracic belt 140, and sacrum belt 150 of torso harness 120, FIG. 1, to be inserted into the horizontal slot and held in place when the torso harness 120 is placed on a user. In general, the sacrum belt 150 of a typical torso harness 120 may have a width of approximately 2.0 inches while the thoracic belt 140 and the connecting strap 126, as well as the other webbing of the torso harness, may have a width of approximately 1.5 inches.

As for the Atlas bar itself, it may be circular or rounded, elliptical, or flat. The Atlas bar and the sheath may be made of metal, wood, bamboo, fabric, plastic (i.e., ultra-high molecular weight polyethylene, polypropylene, polytetraflouroethylene, high-density polyethylene, and polyurethane), fiberglass, carbon fiber, foam (high-, medium-, or low-density, i.e., EVA/polyolefin, polyurethane), etc. The Atlas pads may be made of rubber, fabric, foam (high-, medium-, or low-density, i.e., EVA/polyolefin), plastic (i.e., ultra-high molecular weight polyethylene, polypropylene, polytetraflouroethylene, high-density polyethylene, low-density polyethylene, and polyurethane), poly vinyl chloride gel, leather, etc., and the like.

FIG. 5a shows a top plan view of the Atlas sheath 402 shown in FIG. 4. Also shown in this view is the locking key assembly 404a which is configured to hold a sheath locking key 404, FIG. 4 that allows an Atlas bar to be movably adjusted in Atlas sheath 402. FIG. 5b shows a side elevation view of the example of the Atlas sheath shown in FIG. 5a, which includes strap slide 410c, comprising a slot having a width which allows insertion of webbing having widths of 1½-2 inches (see FIG. 15c).

Figure 6A:
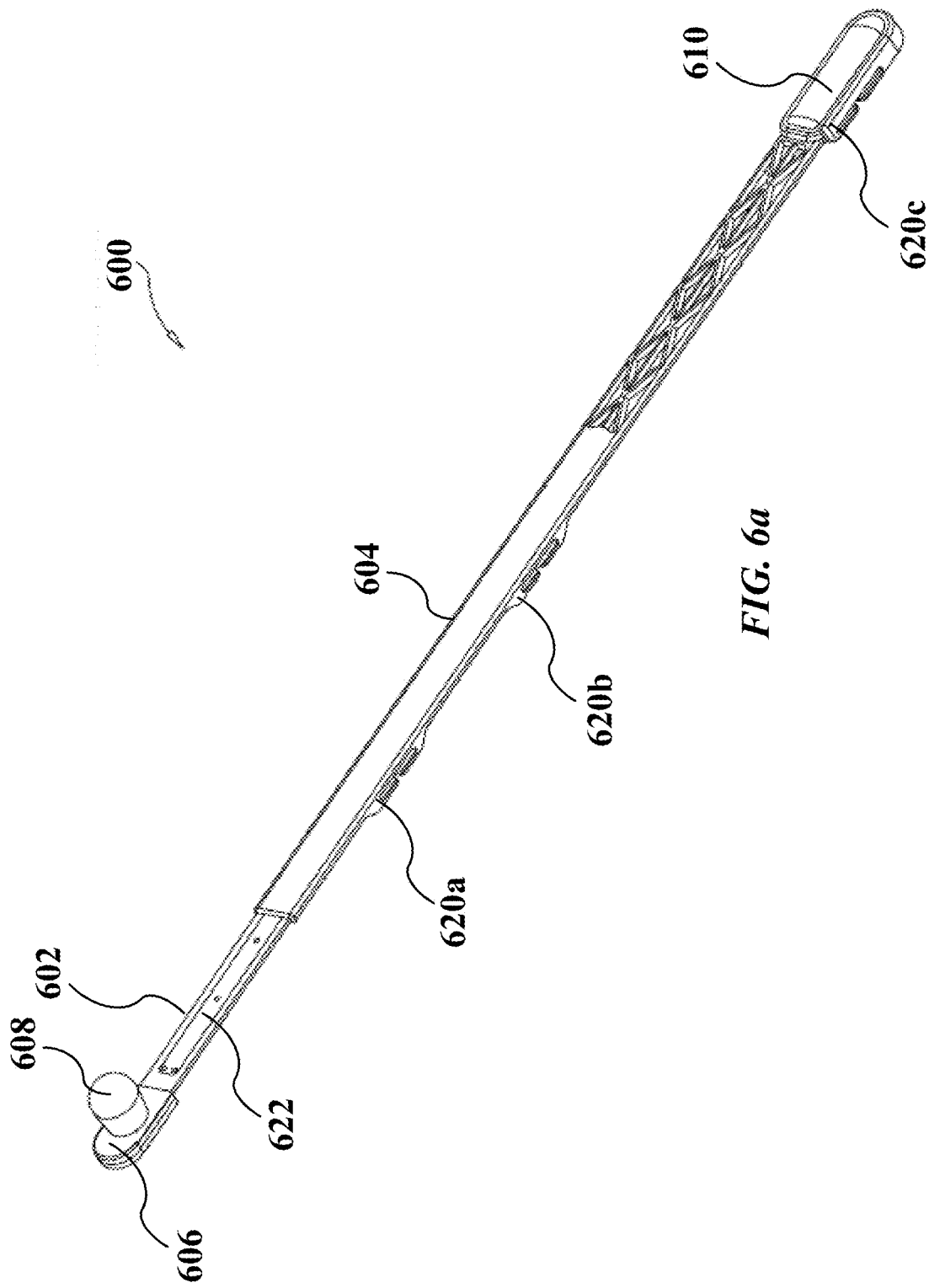
FIG. 6a shows a front perspective view of an example of an adjustable measuring and spinal alignment device comprising an Atlas bar with an Atlas pad and an Atlas sheath with a sacrum pad into which the Atlas bar is inserted in accordance with the invention.

FIG. 6a shows a front perspective view of an example of an adjustable measuring and spinal alignment device 600 comprising an Atlas bar 602 and an Atlas sheath 604 into which the Atlas bar 602 is inserted in accordance with the invention. Atlas bar 602 is shown with an Atlas pad assembly 606 that may be placed at the top of the Atlas bar 602 and an Atlas pad 608 affixed to the Atlas pad assembly 606. In the example, Atlas pad 608 may be made of foam and have a diameter of 1.65 inches and a length of 38.0 mm.

Atlas sheath 604 may include a sacrum pad 610 that when the adjustable measuring and spinal alignment device 600 is placed on the spine of a user, the sacrum pad 610 will be placed on the center of the sacrum of the user. Atlas sheath 604 may also include strap slides 620a, 620b, and 620c, each of which are configured to receive (through a slit in the strap slide) and hold in a slot of each strap slide a belt or webbing of a torso harness designed to hold the adjustable measuring and spinal alignment device 600 against the spine of a user. Strap slide 620c is configured to hold a sacrum belt 150 of a torso harness 120, FIG. 1, and strap slides 620b and 620a are configured to hold thoracic belt 140 and connecting strap 126, FIG. 1, respectively. With thoracic belt 140 and connecting strap 126, FIG. 1, inserted into the slots of strap slides 620b and 620a, FIG. 1, respectively, the Atlas sheath 604 holding the Atlas bar 602 will thus be in contact with the center of the thoracic region of the user's spine. Magnetic strip 622 is inserted in the Atlas bar 602 and may be used in adjustment of the Atlas bar 602 within the Atlas bar 604.

Figure 6B:
Figure 6C:

FIG. 6b shows a front elevation view of the adjustable measuring and spinal alignment device 600 shown in FIG. 6a and FIG. 6c shows a side elevation view of the adjustable measuring and spinal alignment device 600 shown in FIG. 6a.

FIG. 7a shows a rear elevation view of an example implementation of an unconnected sacrum belt 7700 in accordance with the invention. Sacrum belt 7700 may include a slide release-receptor 704 and a slide release-tang 706, where a user may fasten the sacrum belt 7700 around his waist by inserting the slide release-tang 706 into the slide release-receptor 704. Also shown are 37 mm buckle 710*a* and 37 mm buckle 710*b*, which may be connected to the bottom ends of the right-shoulder suspender 122 (FIG. 1) and the left-shoulder suspender 124 (FIG. 1), respectively, when assembling a torso harness. The width 710 of sacrum belt 7700 may be approximately 2.0 inches.

FIG. 7*b* shows a top plan of the sacrum belt 700 shown in FIG. 7*a*.

Figure 8:
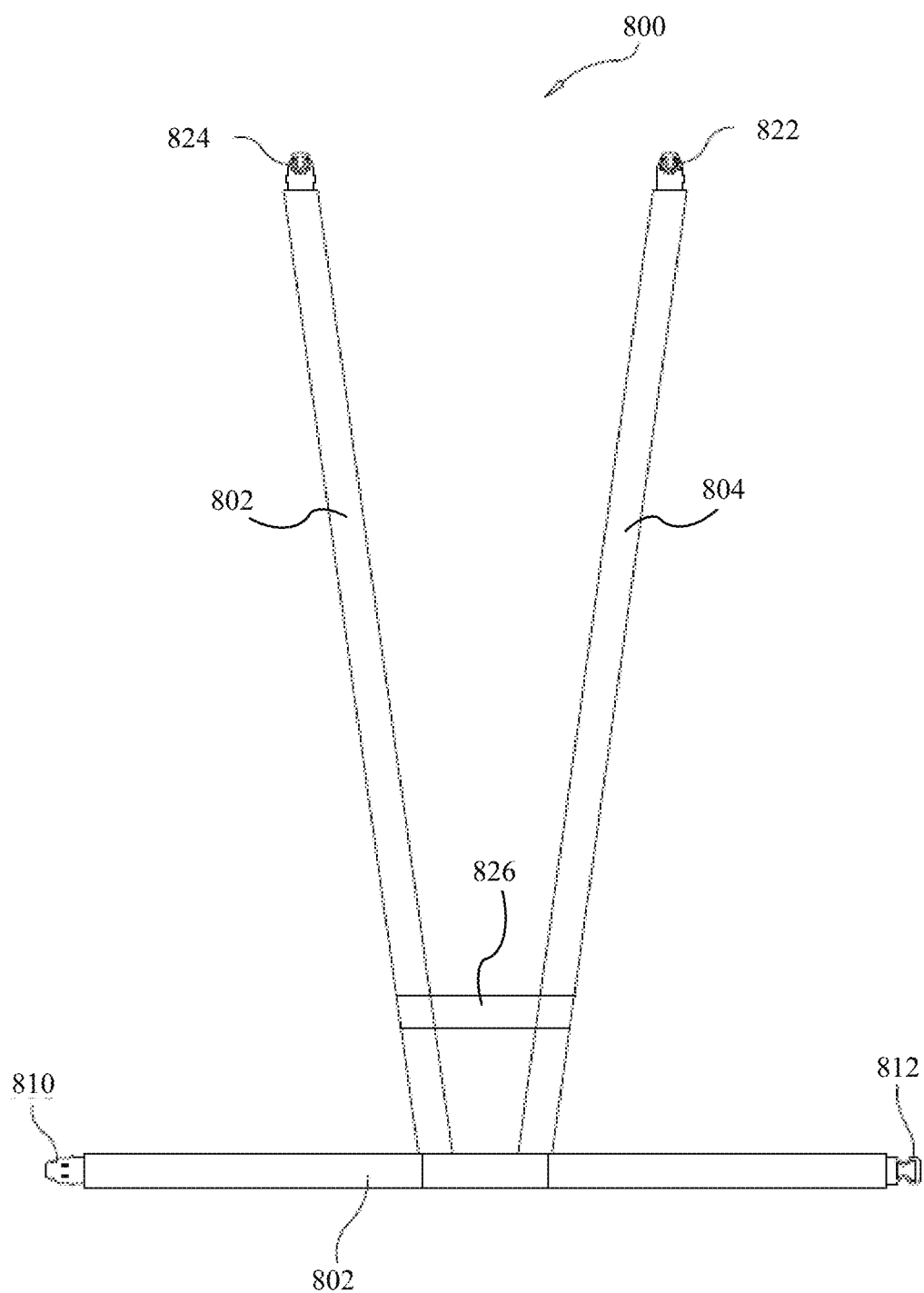
FIG. 8 shows a rear elevation view of an example implementation of a thoracic belt together with a left-shoulder and a right-shoulder suspender in accordance with the invention that is unconnected.

FIG. 8 shows a rear elevation view of an example implementation of an unconnected thoracic belt 800 comprising a left-shoulder and right-shoulder suspender in accordance with the invention. In general, the webbing shown in this rear elevation view is the upper half of the torso harness 120, FIG. 1, comprising a thoracic belt 800, together with a left-shoulder suspender 802 and a right-shoulder suspender 804. The thoracic belt 800 may include a slide release-receptor 810 and a slide release-tang 812, where a user may fasten the thoracic belt 800 around his midriff by inserting the slide release-tang 812 into the slide release-receptor 810. Once the thoracic belt 800 is connected around the user's midriff, the left-shoulder suspender 802 may be placed over the left shoulder of the user and the right-shoulder suspender 604 over the right shoulder, with the ends of the left-shoulder suspender 814 and the right-shoulder suspender 812 connected to the sacrum belt 150, FIG. 1, with 38 mm buckles 820 and 822, respectively.

The thoracic belt 800 shown in FIG. 8 may also include a connecting strap 826 that connects the left-shoulder suspender 802 and the right-shoulder suspender 804. Also, the left-shoulder suspender 802 and the right-shoulder suspender 804 may also be connected to the front of the thoracic belt 800 using 38 mm buckles 820 and 822, respectively, after these suspenders have been placed over the shoulders of a user. As for the webbing of a torso harness, in a preferred embodiment the sacrum belt 802 may have a width of 2.0 inches while the remaining webbing of the torso harness may have widths of 1½-2 inches. In contrast to the torso harness of FIG. 1, in FIG. 8 the left-shoulder suspender 802 and the right-shoulder suspender 804 are stitched onto or heat fused into the sacrum belt 800 rather than connected with cam or spring buckles.

Figure 9A:
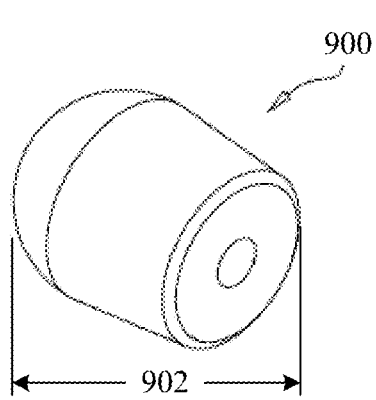
FIG. 9a shows an example of a medium neoprene foam Atlas pad in accordance with the invention having a length of 38.0 mm.
Figure 9B:
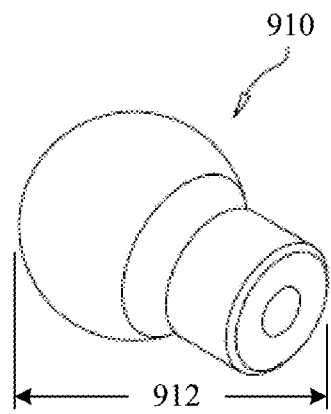
FIG. 9b shows another example of a medium neoprene foam Atlas pad in accordance with the invention having a length of 45.0 mm.
Figure 9C:
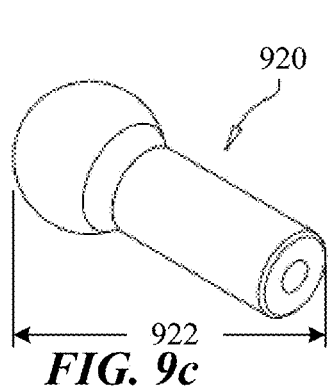
FIG. 9c shows yet another example of a medium neoprene foam Atlas pad in accordance with the invention having a length of 76.0 mm.

FIG. 9*a* shows an example of a medium neoprene foam Atlas pad 900 in accordance with the invention having a length 902 of 38.0 mm. The FIG. 9*b* shows another example of a medium neoprene foam Atlas pad 99 in accordance with the invention having a length 912 of 45.0 mm. FIG. 9*c* shows yet another example of a medium neoprene foam Atlas pad 920 in accordance with the invention having a length 922 of 76.0 mm. The knob at the end of each of FIGS. 9*a*, 9*b*, and 9*c* has a diameter of 32.0 mm.

Figure 9D:
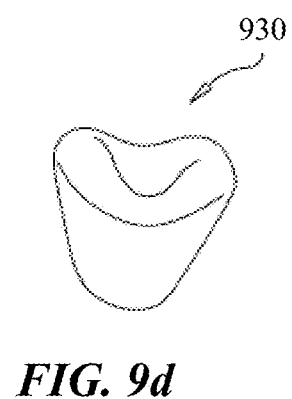
FIG. 9d shows yet another example of an Atlas pad in accordance with the invention having a different shape than that of FIG. 9a, FIG. 9b, and FIG. 9c.
Figure 9E:
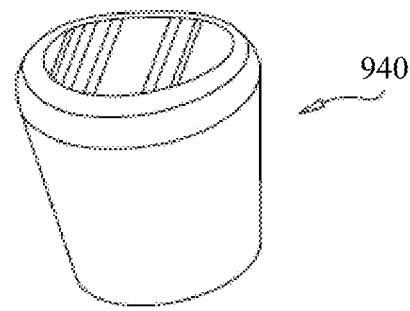
FIG. 9e shows yet another example of an Atlas pad in accordance with the invention having yet another different shape than that of FIG. 9a, FIGS. 9b, 9c, and FIG. 9d.

FIG. 9*d* shows another example of an Atlas pad in accordance with the invention having different dimensions and shape than that of FIG. 9*a*, FIG. 9*b*, and FIG. 9*c* and FIG. 9*e* shows yet another example of an Atlas pad in accordance with the invention having yet other different dimensions and shape than that of FIGS. 9*a*, 9*b*, 9*c*, and 9*d*. All of the pads of FIGS. 9*a*, 9*b*, 9*c*, 9*d*, and 9*e* are removable and adjustable in that each may be removed and replaced by other Atlas pads of varying dimensions, shapes, and materials selected by the user (see FIG. 2).

Figure 10A:
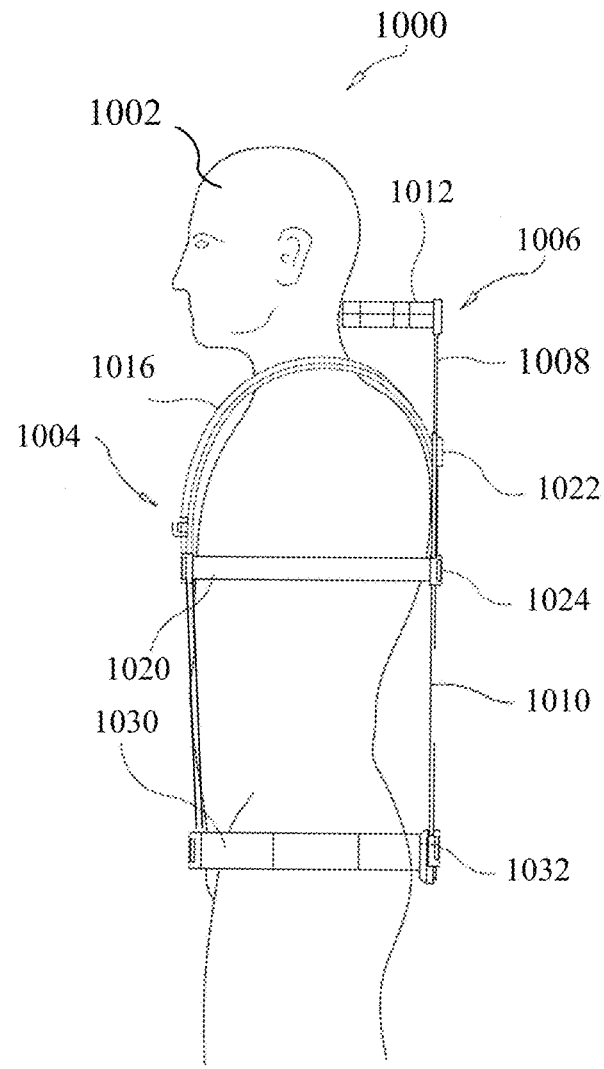
FIG. 10a shows a side elevation view of a schematic sketch of a mannequin torso wearing a torso harness holding an Atlas bar and an Atlas sheath.

FIG. 10*a* shows a side elevation view of a schematic sketch 1000 of a torso mannequin 1002 wearing a torso harness 1004 holding an adjustable measuring and spinal alignment device 1006 in accordance with the invention comprising an Atlas bar 1008 and an Atlas sheath 1010 into which the Atlas bar 1008 is inserted. The Atlas bar 1008 includes an Atlas pad 1012 which is shown placed against the back of the torso mannequin 1002 below the head of a user at the Atlas vertebra of the user.

The torso harness 1004 may also include a left suspender 1016 and a right-shoulder suspender (not shown), a thoracic belt 1020 and a sacrum belt 1030. The left-shoulder suspender 1012 and the right-shoulder suspender (not shown) may be connected by a connecting strap (not shown). Strap slide 1022 is shown attached to the connecting strap (not shown) and strap slide 1024 is shown attached to the thoracic belt 1020, where strap slide 1022 and strap slide 1024 cause the Atlas sheath 1010 to come in contact with the thoracic region of a user's spine. Likewise, sacrum pad 1032 is shown placed on the center of the sacrum of the torso mannequin 1002 and held in place by the sacrum belt 1030 when it is connected around the sacrum of a user.

Figure 10B:
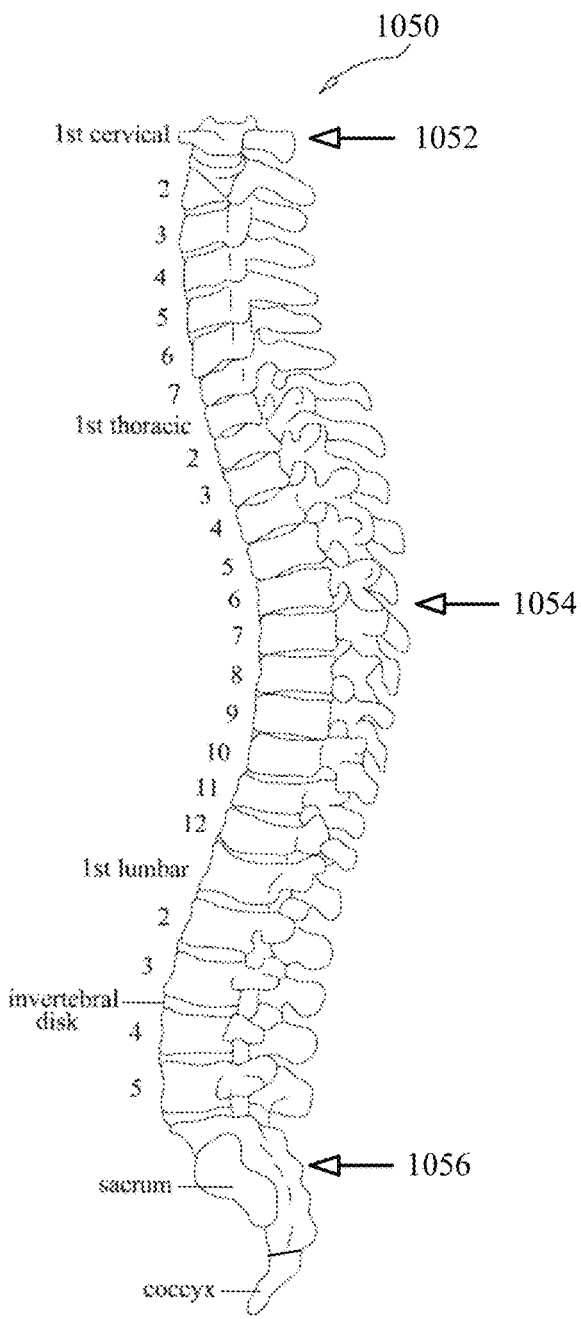
FIG. 10b shows a side elevation view of a schematic sketch of the human spine with indications of the specific vertebrae or regions of the spine that are in contact with an Atlas bar or an Atlas sheath when worn by a user with a torso harness.

FIG. 10*b* shows a side elevation view of a schematic sketch 1050 of the human spine with indications of the specific vertebra or region of the spine that are in contact with an Atlas bar and Atlas sheath when worn by a user with a torso harness. Arrow 1052 indicates the Atlas vertebra which is the contact point of the Atlas pad 1012 of the Atlas bar 1008. Arrow 1054 indicates the thoracic region of a user's spine that is in contact with that portion of the sheath between strap slide 1022 and strap slide 1024. Arrow 1056 indicates the center of the sacrum of a user's spine that is in contact with the sacrum pad 1032 that is positioned at the inside bottom of the Atlas sheath 1010 into which the Atlas bar 1008 is inserted, where the sacrum consists of five fused vertebrae located between the lumbar region of the spine and the coccyx (or tailbone) of the spine consisting of four fused vertebrae.

Figure 11:
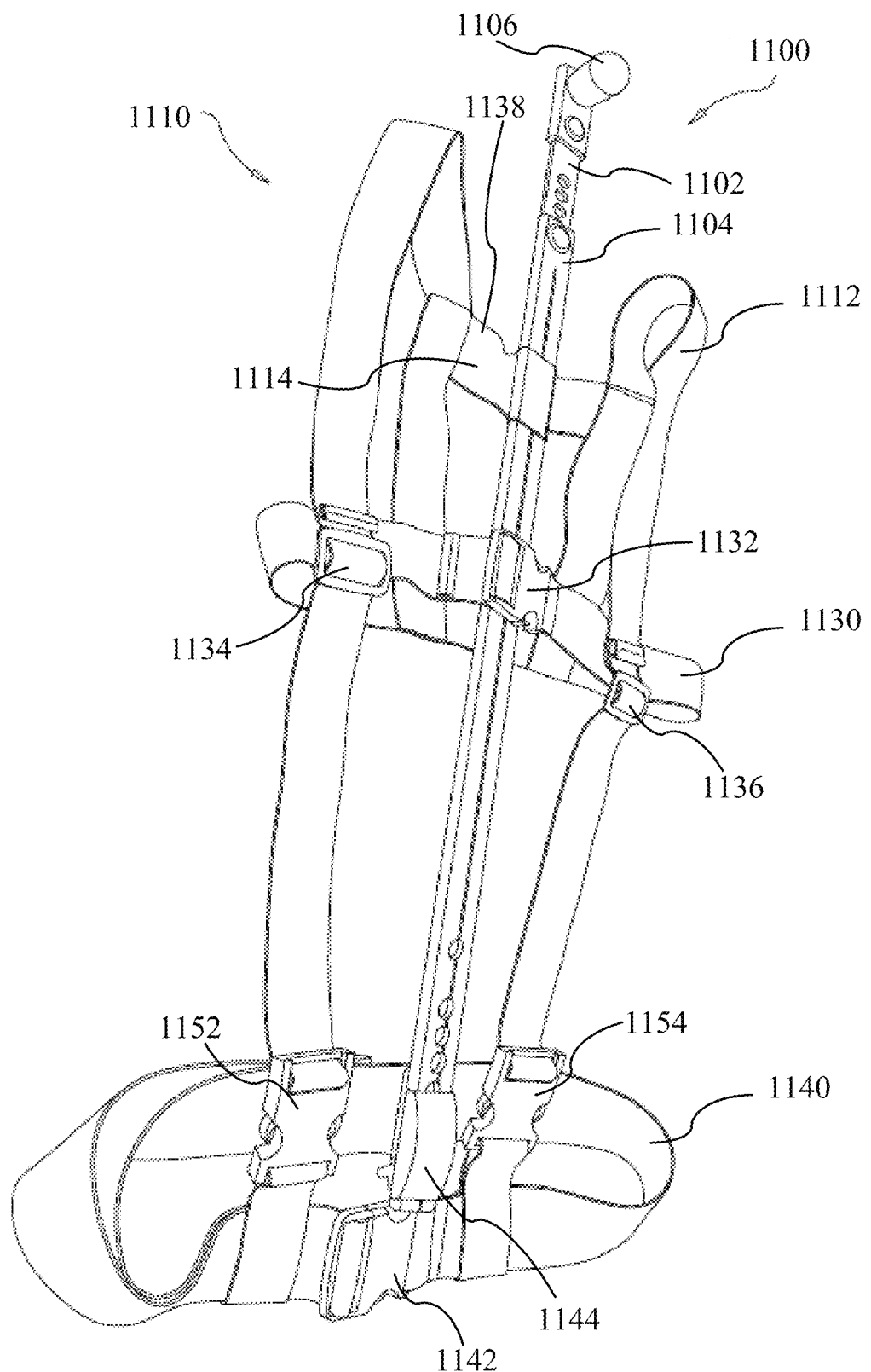
FIG. 11 shows a front perspective view of another example implementation of an assembled adjustable measuring and spinal alignment apparatus in accordance with the invention, comprising an Atlas bar adjustably inserted into an Atlas sheath and a torso harness configured to hold the Atlas bar and the Atlas sheath against the spine of the user, where the assembled adjustable measuring and spinal alignment apparatus is placed on a flat surface.

FIG. 11 shows a front perspective view of another example implementation of an assembled adjustable measuring and spinal alignment apparatus 1100 in accordance with the invention, comprising an Atlas bar 1102 adjustably inserted into a sheath 1104 and a torso harness 1110 configured to hold the Atlas bar 1102 and sheath 1104 against the spine of a user, where the assembled adjustable measuring and spinal alignment apparatus 1100 is placed on a flat surface. The torso harness 1110 comprises a left-shoulder suspender 1112 and a right-shoulder suspender 1114 that are connected by a connecting strap 1138, where one end of connecting strap 1138 may be sewn or heat fused into left-shoulder suspender 1112 and the other end of connecting strap 1138 likewise may be sewn or heat fused into right-shoulder suspender 1114. The torso harness 1110 also comprises a thoracic belt 1130 and a sacrum belt 1140. One end of the right-shoulder suspender 1114 and one end of the left-shoulder suspender 1112 may be connected to the rear of the thoracic belt 1130 with cam or spring buckles (not shown) or sewn or heat fused onto the thoracic belt 1130.

When a user dons torso harness 1110, the left-shoulder suspender 1112 and the right-shoulder suspender 1114 may be placed over the right and the left shoulder, respectively, of the user and then connected to the front of the thoracic belt 1130 with adjustable webbing slider buckles 1136 and 1134, respectively, such that the right-shoulder suspender 1114 and the left-shoulder suspender 1112 will be snugly fitted over the right-shoulder and the left-shoulder, respectively, of a user. Thoracic belt 1130 and sacrum belt 1140 may be fastened by side release buckle 1132 and side release buckle 1142, respectively. Side release buckle 1152 and side release buckle 1154, respectively, are used to connect right-shoulder suspender 1114 and left-shoulder suspender 1112 to the sacrum belt 1140 in lieu of cam or spring buckles.

Atlas bar 1102 with a removable and adjustable Atlas pad 1106 is shown adjustably inserted into sheath 1104. Also shown is sacrum pad 1144 positioned at the bottom of sheath 1104. Sheath 1104 may also include slide straps positioned on the sheath 1104 (see FIG. 16 for an example) where these strap slides may be used to attach the sheath 1104 with inserted Atlas bar 1102 to the connecting strap 1138 (slide strap 1146), the thoracic belt 1130 (slide strap 1148), and the sacrum belt 1140 (slide strap 1150).

Figure 12A:
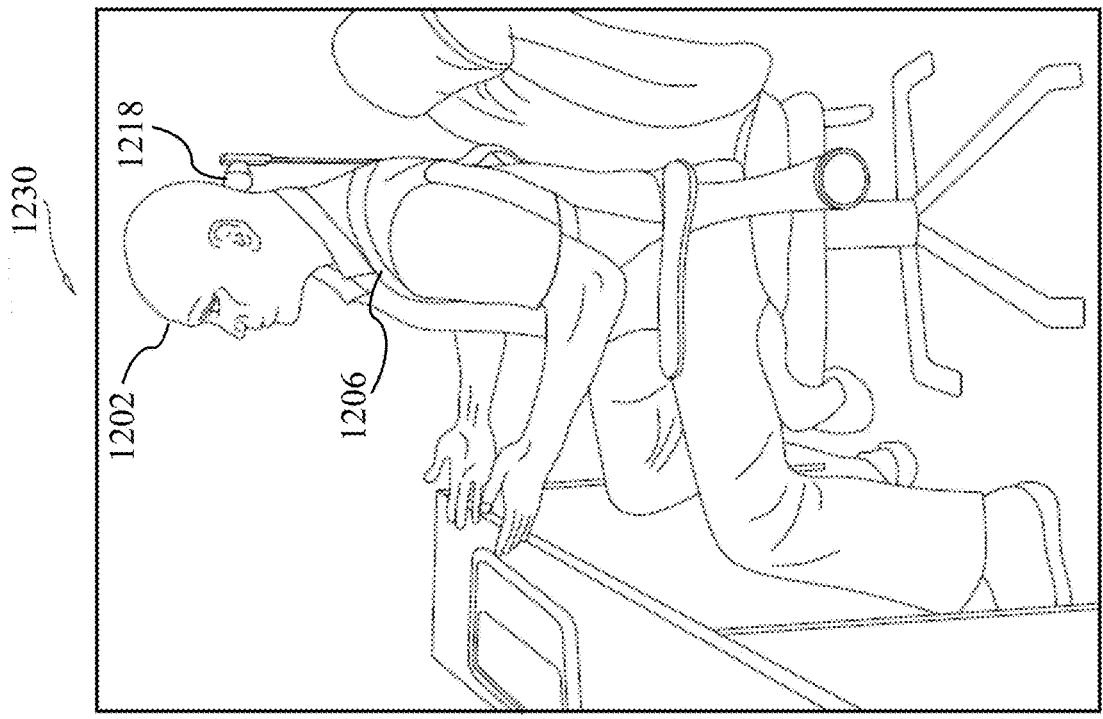
FIG. 12a shows a schematic sketch of a user wearing an adjustable measuring and spinal alignment apparatus in accordance with the invention while working at a computer where the user's sitting posture has resulted in an improper posture.

FIG. 12a shows a schematic sketch 1200 of a user 1202 wearing a torso harness 1206 holding an adjustable measuring and spinal alignment apparatus 1210 in accordance with the present invention while working at a computer where the user's sitting posture has resulted in an improper posture. In this schematic sketch, the user 1202 is wearing a torso harness 1206 that holds an Atlas sheath 1214 with an Atlas bar 1216 with an Atlas pad 1218 inserted thereon. Schematic sketch 1200 shows a gap 1220 between the Atlas pad 1218 and the Atlas vertebra of the user 1202. The reason for this is that while the adjustable measuring and spinal alignment apparatus was initially set up properly with the Atlas pad 1218 in contact with the center of the Atlas vertebra of the user and the Atlas sheath 1214 in contact with the center of the thoracic region of the spine of the user and the sacrum pad (not shown) in contact with the center of the sacrum of the user, the user while working at his computer for an extended period of time has tended to bring his head forward to look downward at a computer screen thus causing stress to his neck and shoulder muscles. This results in the gap 1220 between the Atlas vertebra of the user and the Atlas pad 1218.

Figure 12B:
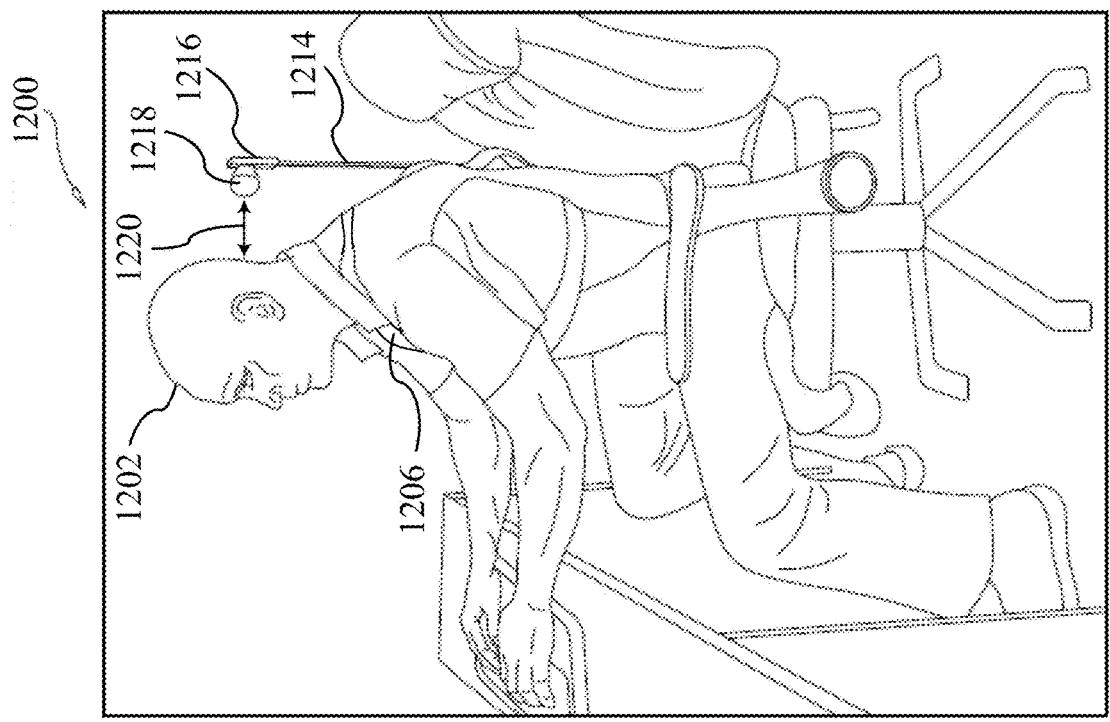
FIG. 12b shows a schematic sketch of the user of FIG. 12a maintaining a proper posture while working at the computer utilizing the measuring and spinal alignment apparatus in accordance with the present invention.

FIG. 12b shows a schematic sketch 1230 of the user 1202 of FIG. 12a maintaining a proper posture while working at the computer wearing a torso harness 1206 holding the measuring and spinal alignment apparatus in accordance with the present invention. Proper posture is maintained because by wearing a properly configured adjustable measuring and spinal alignment apparatus, the user is continuously reminded to feel the pads (and the Atlas sheath) in their correct positions, which activates proper posture and creates new and correct postural habits. In this sketch, the Atlas pad 1218 is shown in contact with the center of the user's Atlas vertebra. By continuously reminding or making a user aware of these points of contact, the adjustable measuring and spinal alignment apparatus has the power to activate correct posture muscles and build correct postural habits while the user is wearing it and will ingrain proper postural memory (i.e., proprioceptive awareness) over time. When either of the Atlas pad 1218 or the sacrum pad (not shown) (or the Atlas sheath) loose contact with the corresponding correct portion of the user's spine (as shown in FIG. 12a), that user is given instant feedback that he or she is out of proper spinal alignment and he or she can make the necessary adjustments to their posture.

Figure 13:
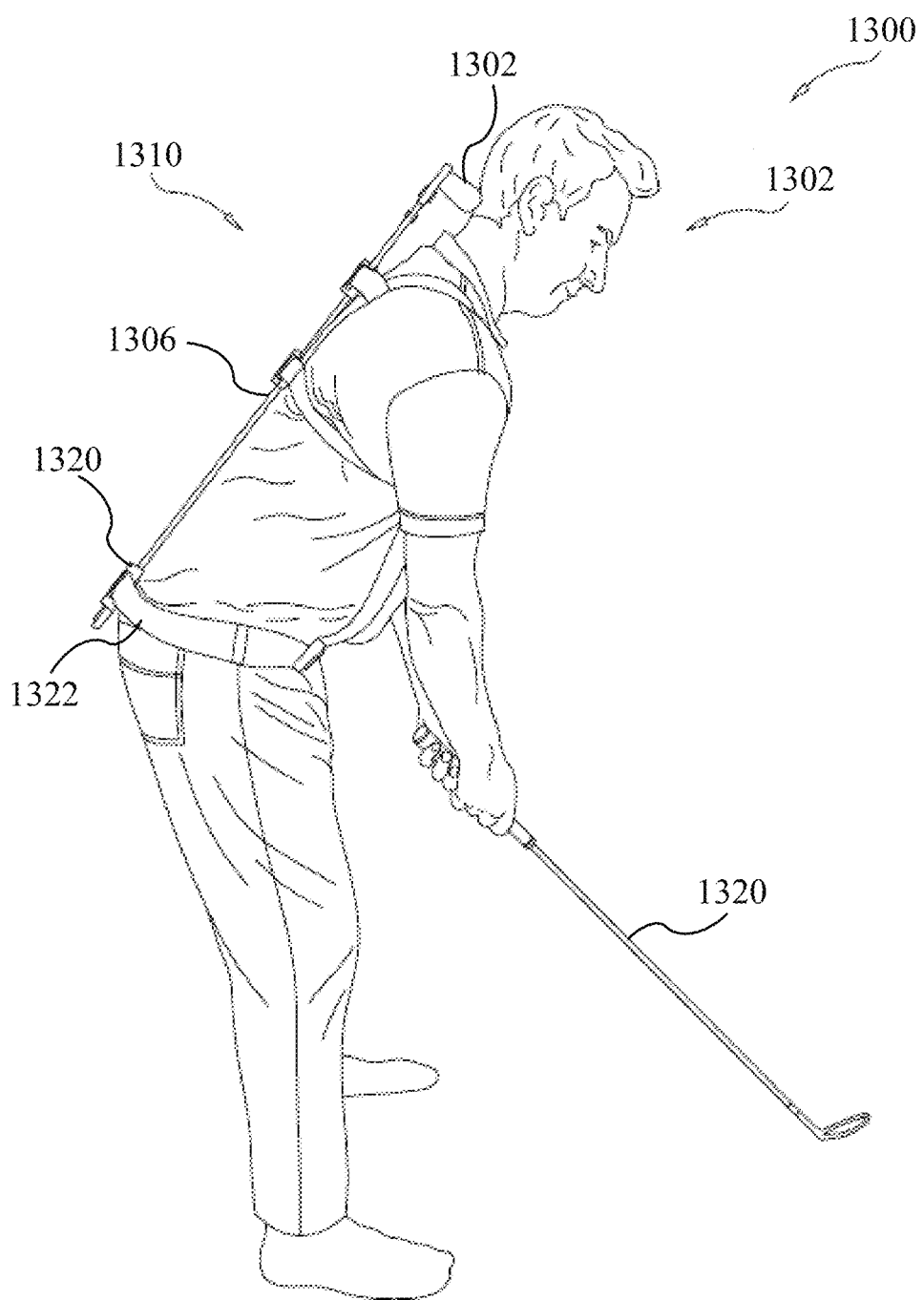
FIG. 13 shows a schematic sketch of a user wearing an adjustable measuring and spinal alignment apparatus in accordance with the invention while holding a golf club and addressing a golf ball.

FIG. 13 shows a schematic sketch of a user 1302 wearing an adjustable measuring and spinal alignment apparatus 1310 in accordance with the invention while holding a golf club and addressing a golf ball. The adjustable measuring and spinal alignment device in this instance is in a setting of a physical activity, e.g., practicing a golf swing, which is a setting that is different than that of standing, walking, or sitting. Accordingly, the configuration and wearing of the adjustable measuring and spinal alignment device may vary to some degree.

Nonetheless, the fundamental concept remains the same. That is, a torso harness is initially set up properly with the Atlas pad 1302 in contact with the Atlas vertebra of the user and the Atlas sheath 1306 in contact with the thoracic region of the spine of the user and the sacrum pad 1320 in contact with the sacrum of the user and held in place by the sacrum belt 1322. In this instance the user is practicing his golf swing and thus make more energetic or strenuous motions than those involved in more stationary activities such as walking or sitting. Throughout the user's practice swings, however, the user must maintain a proper posture while swinging the golf club, and when any of these pads (or the Atlas sheath) loose contact with the corresponding correct portion of the user's spine, the user receives instant feedback that he or she is out of proper spinal alignment and he or she can make the necessary adjustments to their posture and correct their swing. Thus, the measuring and spinal alignment apparatus may be used in numerous non-stationary activities, such as, martial arts, weightlifting, yoga, calisthenics, archery and shooting, ballroom dancing, etc.; in other words, any non-stationary activity where proper posture and form play a not insignificant part.

Figure 14:
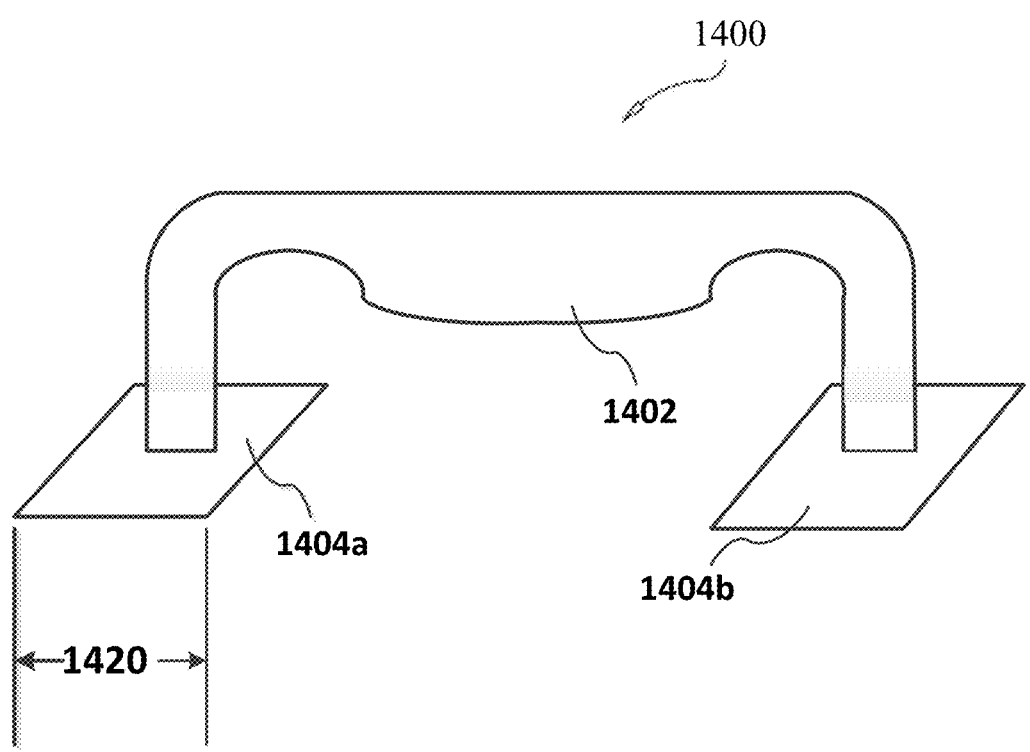
FIG. 14 shows an example of a hand grip that may be attached to an adjustable measuring and spinal alignment device comprising an Atlas bar and an Atlas sheath in accordance with the invention that may be used to facilitate manual operation of the adjustable measuring and spinal alignment device.

FIG. 14 shows an example of a hand grip 1400 that may be attached to an adjustable measuring and spinal alignment device comprising an Atlas bar with an Atlas pad and an Atlas sheath with a sacrum pad in accordance with the invention. Once attached to an adjustable measuring and spinal alignment device, the hand grip 1400 may be used by a third person, such as a physical therapist, personal trainer, spotter, chiropractor, PM&R doctor, etc., to assist a user in improving his posture while performing various exercises and sporting and non-sporting activities, such as, for example, weightlifting, calisthenics, golf, basketball, ballroom dancing, yoga, and the like, by using the hand grip 1400 to place the adjustable measuring and spinal alignment device on or near the user's spine while he or she is performing the exercise or activity to indicate to the user any shortcomings in his or her posture that can be corrected so as to improve the performance of the user.

The hand grip 1400 may contain a handle 1402 having indentations that facilitates a manual operator holding in his or her hand an adjustable measuring and spinal alignment device by gripping the hand grip 1400 once it's been attached to the adjustable measuring and spinal alignment device so that the device can be used to evaluate various activities that may be performed by a user. The hand grip 1400 may also contain two connectors 1404a and 1404a that may be used to attach the hand grip 1400 to an Atlas sheath (not shown) holding an Atlas bar (not shown). In one embodiment the two connectors 1404a and 1404a may be configured to fit into two strap slides affixed to an Atlas sheath.

As another example, in one application the hand grip 1400 may be used by a physical therapist to assist a user by using the adjustable measuring and spinal alignment device to measure the extent of a user's misalignment of his spine and properly configure the Atlas bar and the Atlas sheath for the user. This might entail placing the sacrum pad of an Atlas sheath with an Atlas bar inserted in the Atlas sheath on the center of the sacrum of the user and adjusting the Atlas pad of the Atlas bar until the Atlas pad touches the Atlas vertebra of the user, which determines the proper length of the Atlas bar. This may also determine the proper type of Atlas pad to use as to the shape, length, and material of the pad.

Figure 15A:
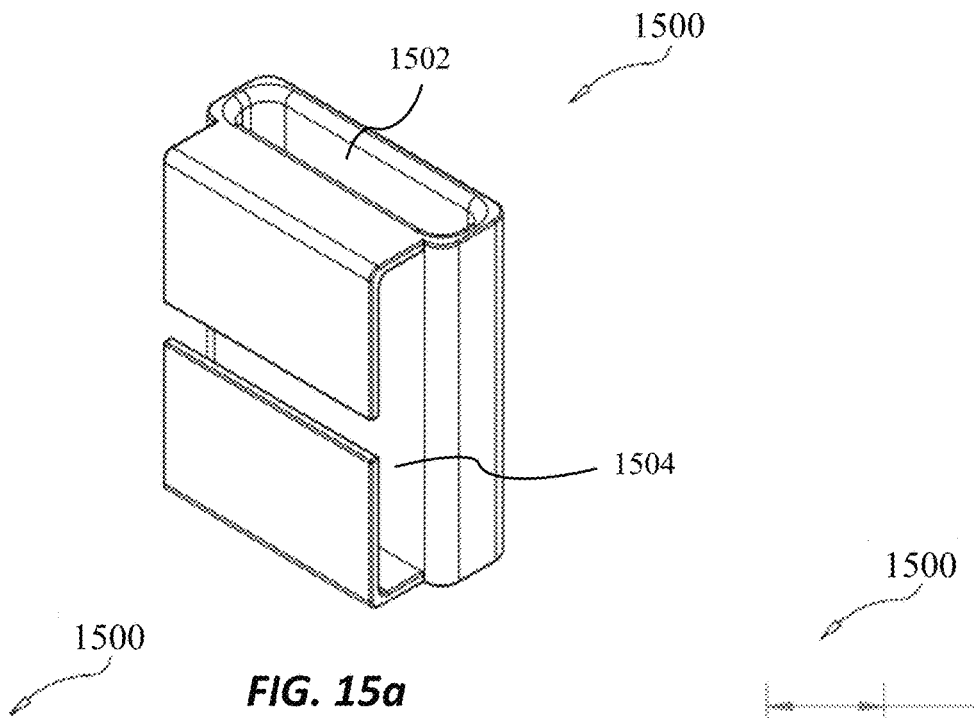
FIG. 15a shows a rear perspective view of a strap slide configured to be fitted over an Atlas sheath of an adjustable measuring and spinal alignment apparatus in accordance with the invention having a horizontal slot configured to receive and hold a belt or strap of a torso harness.

FIG. 15a shows a rear perspective view of a strap slide 1500 configured to be fitted over an Atlas sheath (not shown) of an adjustable measuring and spinal alignment apparatus in accordance with the invention having a horizontal slot configured receive and hold a belt or strap of a torso harness. Examples of movable strap slides used on a torso harness are shown as movable strap slides 128 and 130 in FIG. 1. Strap slide 1500 is shown that includes a vertical slot 1502 and a horizontal slot 1504. Vertical slide 1502 is configured to removably receive an Atlas sheath, after which it may then be moved up or down the Atlas sheath to a desired position. Once in the desired position, a strap or belt may be threaded through the horizontal slot 1504 of strap slide 1500. For example, in FIG. 1, connecting strap 126 is threaded through a horizontal slot of movable strap slide 128 and thoracic belt 140 is threaded through a horizontal slot of movable strap 130.

Figure 15B:
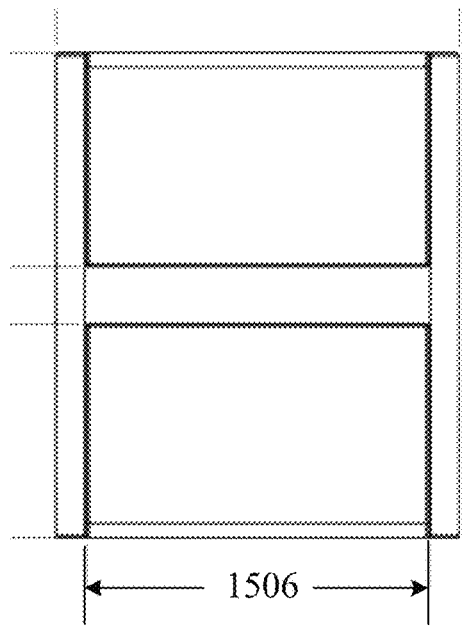
Figure 15C:
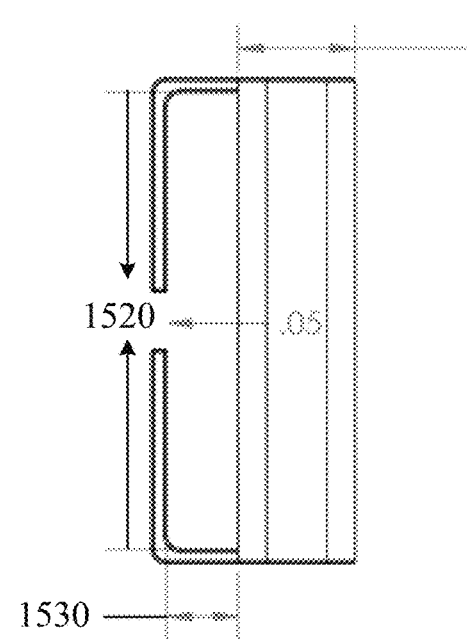

FIG. 15*b* shows a rear elevation view of the strap slide shown in FIG. 15*a* and FIG. 15*c* shows a side elevation view. In FIG. 15*b*, width 1506 may be approximately 1.21" in order to accommodate an Atlas sheath having a width of approximately 1.00". In FIG. 15*c*, length 1520 may be approximately 1.60" and width 1530 may be approximately 0.25", which will accommodate webbing having a width of 1.50".

Figure 16A:
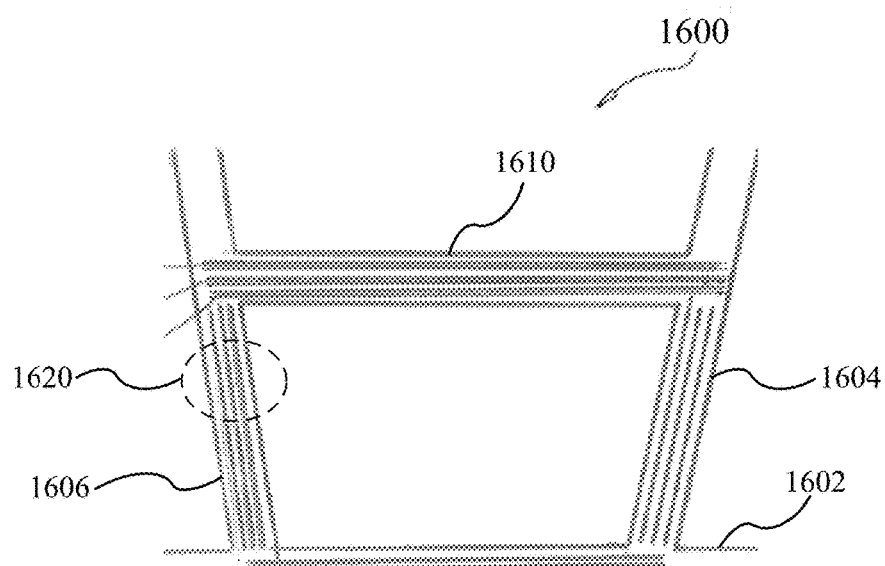
FIG. 16a shows an example of a portion of a thoracic belt webbing of a torso harness configured for holding an adjustable measuring and spinal alignment device in accordance with the invention, where a plurality of rubber inlays are stitched onto the inside of the thoracic belt webbing to facilitate and enhance the adhesion and stability of the torso harness on the user.

FIG. 16*a* shows an example of a portion of a thoracic belt webbing 1600 of a torso harness configured for holding an adjustable measuring and spinal alignment device in accordance with the invention. Thoracic belt webbing 1600 compromises a portion of a thoracic belt 1602, a portion of a right-shoulder suspender 1604, a portion of a left-shoulder suspender 1606, and a connecting strap 1610 of a torso harness (see, for example, FIG. 8). FIG. 16*a* shows these portions each embroidered with a plurality of rubber inlays 1620 that are stitched onto the corresponding portions of the embroidered thoracic belt webbing 1600, where the thoracic belt webbing 1600 with embroidery forms an isosceles trapezoid. This embroidered isosceles trapezoid is formed on the inside of the thoracic belt of a torso harness, i.e., that side of the torso harness that comes in contact with the back of a user, and its purpose is to provide a moderate amount of friction that facilitates and enhances the adhesion and stability of the torso harness on the user.

Figure 16B:
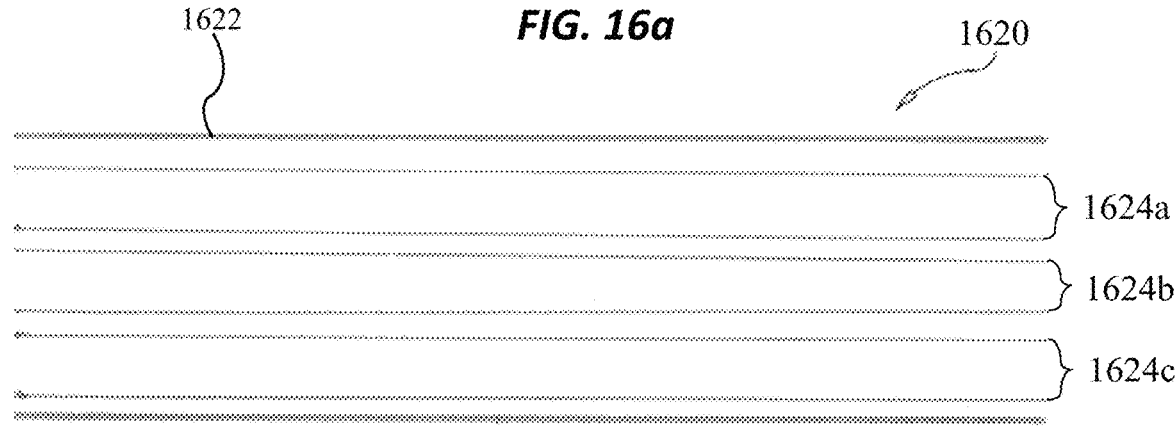
FIG. 16b shows an example of a portion of a sacrum belt of a torso harness configured for holding an adjustable measuring and spinal alignment device in accordance with the invention having a plurality of rubber inlays stitched onto the inside of the sacrum belt.

FIG. 16*b* shows an example of a portion 1602 of a portion 1602 of a sacrum belt 1600 of a torso harness configured for holding an adjustable measuring and spinal alignment device in accordance with the invention. FIG. 16*b* shows portion 1602 of the sacrum belt 1600 embroidered with a plurality of rubber inlays 1624*a*, 1624*b*, and 1624*c* that are stitched lengthwise along the inside of sacrum belt 1600. Like thoracic belt webbing 1600, the purpose of rubber inlays 1624*a*, 1624*b*, and 1624*c* is to enhance the adhesion and stability of the sacrum belt around the lower waist of the user.

Figure 16C:
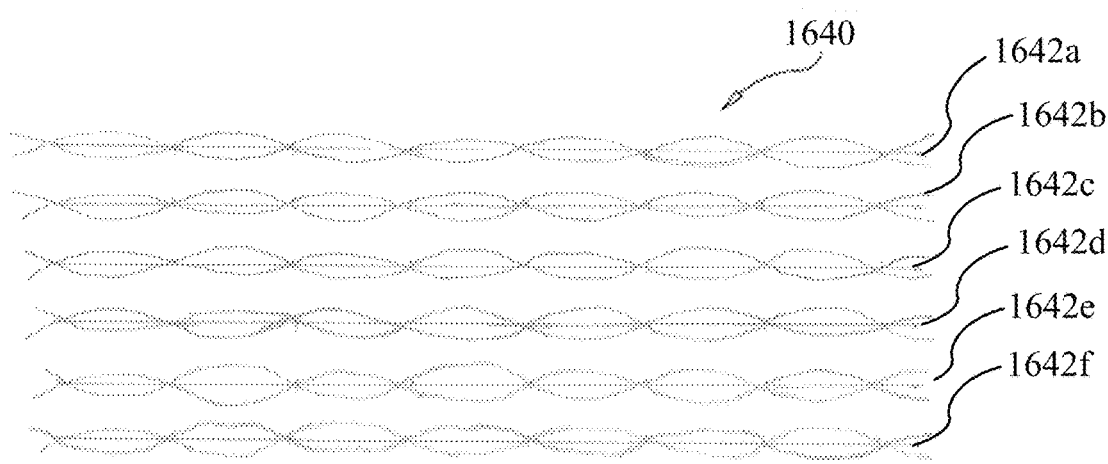
FIG. 16c shows a sketch of an example of the rubber inlays that are shown in FIGS. 16a and 16b.

FIG. 16*c* shows a sketch of an example of the rubber inlay 1640 that is shown in FIGS. 16*a* and 16*b*, where rubber inlay 1640 comprises six strands 1642*a*, 1642*b*, 1642*c*, 1642*d*, 1642*e*, and 1642*f*. In general, each rubber inlay comprises multiple-string inter-twined strands where each multiple-string may include three to nine 1 mm diameter elastic rubber strings. In FIG. 16*c* rubber inlay 1640 is shown with six strands with each strand consisting of three inter-twined 1 mm diameter elastic rubber strings. In other embodiments a rubber inlay may include five to eight embroidered strands placed side by side as shown in in FIGS. 16*a* and 16*b*.

Figure 17:
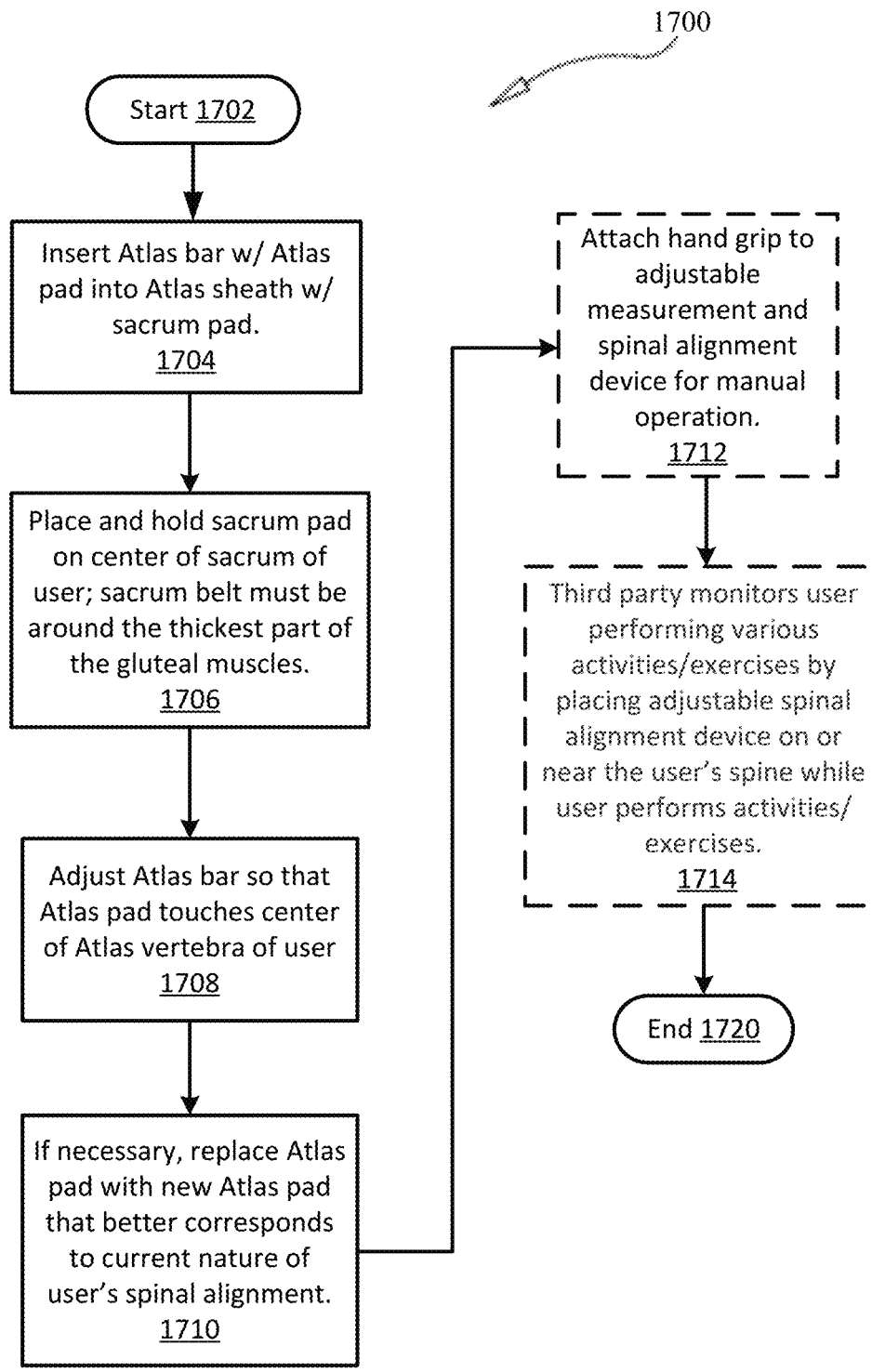
FIG. 17 shows a flowchart illustrating an example of a method of fitting an Atlas bar and an Atlas sheath in accordance with the invention against the spine of a user and then using the Atlas bar to measure the condition of the user's spine.

FIG. 17 shows a flowchart illustrating an example of a method of fitting an Atlas bar and an Atlas sheath in accordance with the invention against the spine of a user and then using the Atlas bar to measure the condition of the user's spine. The method 1700 starts at step 1702 and next, in step 1704 an Atlas bar with an Atlas pad is inserted into an Atlas sheath with a sacrum pad. In step 1706 the process of configuring the Atlas bar and Atlas sheath begins by placing the sacrum pad of the Atlas sheath on the center of the sacrum of the user. The sacrum pad may be held in place manually or with a sacrum belt placed around the thickest part of the user's gluteal muscles, about even with the greater trochanters of the user's femurs on the side of the user's pelvis; in other words, this is a few inches below where a user would normally wear a waist belt.

In step 1708, the Atlas bar is adjusted, and then set in place, so that the Atlas pad touches the center of the Atlas vertebra of user. This step fixes the proper length of the Atlas bar and the Atlas sheath for subsequent usage. In step 1710, if necessary, the Atlas pad initially used for setup may be replaced with a new Atlas pad that better corresponds to the nature of user's spinal alignment determined after placing the Atlas pad at the Atlas vertebra of the user.

In optional step 1712, a hand grip is attached to the adjustable measurement and spinal alignment device for manual operation, whereby a third party may monitor or assist a user performing various activities or exercises by placing the adjustable measurement and spinal alignment device on or near the user's spine while the user performs the activities or exercises so as to make the user self-aware of any improper spinal alignment. These activities and/or exercises are performed in optional step 1714, and when completed the process ends at step 1720.

Figure 18:
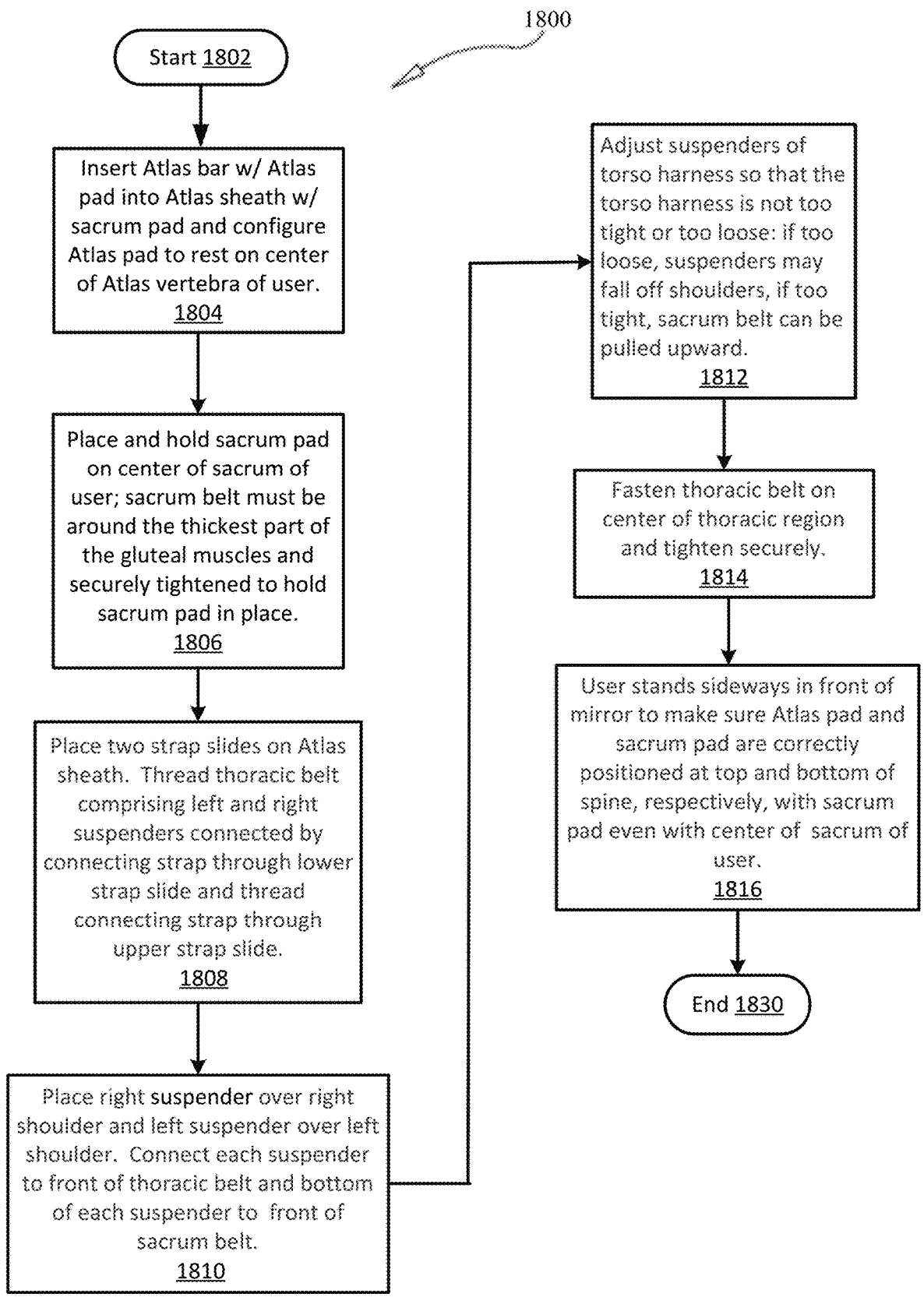
FIG. 18 shows a flowchart illustrating an example of a method of fitting and adjusting a torso harness holding an Atlas bar and an Atlas sheath in accordance with the invention against the spine of a user and then having the user perform various activities while having the Atlas bar pressed against the spine of the user.

FIG. 18 shows a flowchart illustrating an example of a method of fitting and adjusting a torso harness holding an Atlas bar and an Atlas sheath in accordance with the invention against the spine of a user and then having the user perform various activities while having the Atlas bar and Atlas sheath pressed against the spine of the user. The method 1800 starts at step 1802 and next, in step 1804 an Atlas bar with an Atlas pad is inserted into an Atlas sheath with a sacrum pad and configured so as to have the sacrum pad placed on the center of the sacrum of the user and the Atlas pad place on the Atlas vertebra of the user when the Atlas bar and Atlas sheath are pressed against the spine of the user. This step consists of steps 1604-1610 of method 1600, FIG. 16, and relates to proper configuration of an Atlas bar and sheath.

In step 1806 the sacrum pad of the Atlas sheath is placed on the center of the sacrum of the user and firmly held in place by a sacrum belt placed around the thickest part of the user's gluteal muscles, about even with the greater trochanters of the user's femurs on the side of the user's pelvis; in other words, this is a few inches below where a user would normally wear a waist belt. (Note: Because the Atlas bar and the Atlas sheath have been previously properly configured, the Atlas pad of the Atlas bar will necessarily be placed at the Atlas vertebra of the user.

Turning to step 1808, two strap slides are placed on the Atlas sheath. Next, a thoracic belt comprising a side release buckle and two suspenders (for right and left shoulders) connected by a connecting strap (see, for example, FIG. 9) is threaded through the lower strap slide and the connecting strap is threaded through the upper strap slide. It should be noted that in some embodiments strap slides may be formed directly into an Atlas sheath (see, for example, FIG. 4) in which case strap slides will not be required.

In step 1810, one suspender is placed over the right shoulder and the other is placed over the left shoulder. Each suspender is connected to the front of the thoracic belt and the bottom of each suspender to the front of the sacrum belt. In general, connections between suspenders, the connecting strap, and the thoracic and sacrum belts may be made by sewing or heat fusion, cam or clamp buckles, or side release buckles. Generally, side release buckles are used for fastening and unfastening the thoracic and sacrum belts but may also be used for connecting the suspenders to the thoracic and sacrum belts. The thoracic and sacrum belts and the harness webbing may also include adjustable strap buckles and Tri-bar adjustable webbing sliders where necessary. In step 1812, the suspenders of torso harness are adjusted so that the torso harness is not tight or too loose: if too loose, the suspenders may fall off the shoulders, if too tight, the sacrum belt can be pulled upward. In one embodiment, this adjustment may be done with an adjustable strap buckle or a tri-bar adjustable webbing slider inserted into each suspender.

In step 1814, the thoracic, belt is fastened and adjusted to fit securely around the thoracic region of the user. In step 1816 the user should stand sideways in front of a mirror to make sure the Atlas pad and the sacrum pad are correctly positioned at the top and bottom of the spine, respectively, with the sacrum pad even with the center of the sacrum of the user. The process ends at step 1830 and the user may continue to proceed with his or her planned activities while wearing the torso harness with Atlas bar and Atlas sheath.

The foregoing description of one or more implementations has been presented for purposes of illustration and description. It is not exhaustive and does not limit the claimed inventions to the precise form disclosed. Modifications and variations are possible in light of the above description or may be acquired from practicing the invention.

What is claimed is:

1. A spinal alignment measuring device for measuring, enhancing, and facilitating correct spinal alignment of the spine of a user, the spinal alignmentmeasuring device comprising:
    a straight Atlas bar having a top end, a bottom end, an inside surface, an outside surface, and a removable Atlas pad having an inside end, an outside end, and a length defined by a distance between the inside end and the outside end of the Atlas pad, wherein the outside end of the Atlas pad is perpendicularly placed lengthwise at the top end of the Atlas bar on the inside surface of the Atlas bar;
    wherein the inside end of the Atlas pad is adapted to be placed in physical contact with the center of the Atlas vertebra of the user when the spinal alignment measuring device is in use by the user and whereby the length of the Atlas pad is indicative as a measurement of the misalignment of the user's spine and is selected to be equal to the distance between the center of the Atlas vertebra of the user and the inside surface of the Atlas bar where the Atlas pad is placed; and
    a straight Atlas sheath having a top end, a bottom end, an inside surface, an outside surface, and a sacrum pad placed at the bottom end of the Atlas sheath on the inside surface of the Atlas sheath;
    wherein the Atlas sheath is adapted to adjustably receive and hold the Atlas bar in place and wherein the sacrum pad is adapted to be placed on the spine of the user in alignment with the center of the sacrum of the user;
    wherein whenever a properly adjusted spinal alignment measuring device is placed or affixed along the center line of the user's spine, the inside end of the Atlas pad will be in physical contact with the center of the Atlas vertebra of the user, the inside surface of the Atlas sheath will be in physical contact with the center of the thoracic region of the user's spine, and the sacrum pad will be in physical contact with the center of the sacrum of the user;
    wherein these three physical contact points on the spine of the user may be used to measure the degree of the user's spinal misalignment and create proprioceptive awareness in the user that provides the user with an awareness of a proper posture alignment of the user's spine;
    wherein whenever the spine of the user is altered such that the Atlas pad is no longer in physical contact with the center of the Atlas vertebra, the user will receive instantaneous feedback from the properly adjusted spinal alignment measuring device that he is no longer maintaining proper spinal alignment thus allowing the user to adjust his posture to reacquire proper spinal alignment and to reactivate the user's proprioceptive awareness; and
    wherein whenever the spinal alignment of the user is altered after initial use of the spinal alignment measuring device by the user, the Atlas pad in place may be removed and replaced with a different, second Atlas pad with a modified length equal to a different, second measured distance between the center of the Atlas vertebra of the user's spine in the altered alignment and the inside surface of the Atlas bar.

2. The adjustable spinal alignment measuring device of claim 1, further comprising a torso harness comprising:
    a left-shoulder suspender having a top end and a bottom end and a right-shoulder suspender having a top end and a bottom end;
    a connecting strap connected to the left suspender and to the right-shoulder suspender;
    a thoracic belt connected to the Atlas sheath and configured to be fastened and placed around the user's midriff; and
    a sacrum belt connected to the Atlas sheath and configured to be fastened and placed around the user's hips such that the sacrum pad of the Atlas sheath is placed at the center of the user's sacrum;
    wherein the top end of the left-shoulder suspender and the top end of the right-shoulder suspender are each connected at the front of the thoracic belt; and the bottom end of the left-shoulder suspender and the bottom end of the right-shoulder suspender are each connected at the front of the sacrum belt, and
    whereby the torso harness is used to affix the spinal alignment measuring device at the centerline of the user's torso.

3. The spinal alignment measuring device of claim 2, wherein the torso harness comprises webbing made of nylon, polypropylene, or polyester, with or without a urethane coating.

4. The spinal alignment measuring device of claim 3, further including elastic rubber inlays stitched onto portions of the thoracic belt, the left-shoulder suspender, the right-shoulder suspender, and the connecting strap, where the elastic rubber inlays comprise a plurality of strands each containing a plurality of inter-twined elastic rubber strings.

5. The spinal alignment measuring device of claim 3, wherein the webbing of the sacrum belt of the torso harness has a width of 2.0 inches, and each of the remaining webbing and belts of the torso harness has a width between 1½ and 2.0 inches.

6. The spinal alignment measuring device of claim 5, wherein the thoracic belt and the sacrum belt each contain a side release buckle.

7. The spinal alignment measuring device of claim 6, further comprising a first strap slide having a vertical slot through which the sacrum belt is threaded, a second strap slide having a vertical slot through which the thoracic belt is threaded, and a third strap slide having a vertical slot through which the connecting strap is threaded, wherein each of the first strap slide, the second strap slide, and the third strap slide is configured to movably slide along the Atlas sheath.

8. The spinal alignment measuring device of claim 1, further comprising a vest or jacket comprising:
  a front configured to be opened and closed around the torso of the user;
  a back having a channel configured to receive and hold the Atlas bar and the Atlas sheath;
  a thoracic belt attached to the back of the vest or jacket configured to be fastened and placed securely around the midriff of the user; and
  a sacrum belt attached to the back of the vest or jacket configured to be fastened and placed around the user's hips such that the sacrum pad of the Atlas sheath is placed at the center of the user's sacrum.

9. The spinal alignment measuring device of claim 1, wherein the second Atlas pad is removable and may be replaced with a third Atlas pad with a different length, material, shape, or any combination thereof relative to the first and second Atlas pads, wherein the length of the third Atlas pad is equal to a third measured distance between the center of the Atlas vertebra of the user's spine in a further altered alignment and the inside surface of the Atlas bar.

10. The adjustable spinal alignment measuring device of claim 9, wherein the Atlas pad is made of rubber, fabric, foam (high-, medium-, or low-density), plastic, leather, or poly vinyl gel.

11. The spinal alignment measuring device of claim 1 wherein the Atlas sheath further comprises a cylindrical cavity positioned along a length of the Atlas sheath that is configured to adjustably receive and hold the Atlas bar.

12. The spinal alignment measuring device of claim 11, further including an Atlas pad assembly having a top face and a bottom face, configured to fit securely over the top end of the Atlas bar, and having a hole to receive a threaded pin to hold the Atlas pad.

13. The adjustable spinal alignment measuring device of claim 1, wherein the Atlas pad further comprises:
  a non-supporting knob placed at the inside end of the Atlas pad contoured to conform to and provide physical contact with the center of the Atlas vertebra of the user;
  whereby the outside end of the Atlas pad is configured to receive a threaded pin configured to hold the Atlas pad in place at the inside surface at the top of the Atlas bar.

14. The spinal alignment measuring device of claim 13, wherein the Atlas sheath further comprises a first strap slide having a vertical slot through which the sacrum belt may be threaded, a second strap slide having a vertical slot through which the thoracic belt may be threaded, and a third strap slide having a vertical slot through which the connecting strap may be threaded, wherein each of the first strap slide, the second strap slide, and the third strap slide are formed on an outside surface of the Atlas sheath.

15. The spinal alignment measuring device of claim 1, further comprising a hand grip attachable to the Atlas sheath that facilitates a third party using the adjustable spinal alignment device as a third-party spotter or trainer in conjunction with measuring for a length of the Atlas pad or supervising a user's activities or exercises.

16. A method of configuring and using a spinal alignment measuring device having a straight Atlas bar having a top end, a bottom end, an inside surface, an outside surface, and a removable Atlas pad having an inside end, an outside end, and a length defined by the distance between its inside end and its outside end, wherein the outside end of the Atlas pad is adapted to be removably attached to the inside surface at the top end of the Atlas bar, and an Atlas sheath having a top end, a bottom end, an inside surface, an outside surface, and a sacrum pad placed on the inside surface at the bottom end of the Atlas sheath, the Atlas sheath is straight, the method comprising:
  placing the sacrum pad of the Atlas sheath on the center of the sacrum of a user;
  holding the sacrum pad firmly in place manually or with a sacrum belt connected at the bottom end of the Atlas sheath and placed and fastened around the thickest part of the user's gluteal muscles;
  inserting the Atlas bar in the top end of the Atlas sheath;
  adjusting the Atlas bar in the Atlas sheath so that the inside end of the Atlas pad is in alignment with the center of the Atlas vertebra of the user and the inside surface of the Atlas sheath is in physical contact with the center of the thoracic region of the user's spine with a thoracic belt connected to the Atlas sheath;
  locking the Atlas bar in place using a locking assembly of the Atlas sheath;
  selecting the Atlas pad having a length equal to the distance between the center of the Atlas vertebra of the user and the inside surface of the Atlas bar where the Atlas pad is removably attached;
  removably attaching the selected Atlas pad to the inside surface at the top end of the Atlas bar; and
  wherein whenever a properly adjusted spinal alignment measuring device is placed or affixed along the center line of the user's spine, these three physical contact points on the spine of the user create proprioceptive awareness in the user that provides the user with an awareness of a proper alignment of his spine; and
  wherein whenever the spinal alignment of the user has changed after initial use of the spinal alignment measuring device by the user, the Atlas pad in place may be removed and replaced with a new Atlas pad of a modified length, wherein the modified length is equal to a new measured distance between the center of the Atlas vertebra of the user's spine in the changed alignment and the inside surface of the Atlas bar.

17. The method of configuring and using the spinal alignment measuring device claim 16, further comprising the steps of:
  fitting and adjusting a torso harness holding the Atlas bar and the Atlas sheath against along the center line of the spine of the user;
  placing and fastening a thoracic belt connected to the Atlas sheath, comprising a side release buckle and a left suspender and a right suspender connected by a connecting strap around the midriff of the user;
  placing the right suspender over the right shoulder of the user and the left suspender over the left shoulder;
  connecting the right suspender to the thoracic belt to the right of the side release buckle and the left suspender to the left of the side release buckle;
  connecting the end of the right suspender to the sacrum belt on the right of the side release buckle and the end of the left suspender on the left of the side release buckle; and adjusting the right suspender and the left suspender of the torso harness so that the torso harness is configured to firmly hold the spinal alignment measuring device along a centerline of the torso of the user during an intended activity.

18. The method of configuring and using the spinal alignment measuring device of claim 17, wherein the step of adjusting the right suspender and the left suspender of the torso harness includes adjusting an adjustable strap or a tri-bar adjustable webbing slider inserted in each of the right suspender and the left suspender.

19. The method of configuring and using the spinal alignment measuring device of claim 17, wherein the webbing of the sacrum belt of the torso harness has a width of 2.0 inches, and each of the remaining webbing and belts of the torso harness have widths between 1½ and 2.0 inches.

20. The method of configuring and using the spinal alignment measuring device of claim 17, wherein the locking assembly of the Atlas sheath includes a magnetic strip, a sheath-locking-key magnet, and a plastic locking key.

21. The method of configuring and using the spinal alignment measuring device of claim 16, wherein the step of selecting the Atlas pad includes:
  attaching a hand grip to an assembled Atlas bar and Atlas sheath such that a third party can easily maneuver the assembled Atlas bar and Atlas sheath on or near the user's spine in order to measure the user's spinal alignment or to assist the user in performing various activities or exercises;
  using the hand grip, placing the sacrum pad of the configured and assembled Atlas bar and Atlas sheath by the third party on the center of the sacrum of the user;
  measuring the distance between the center of the Atlas vertebra of the user and the inside surface of the Atlas bar where the Atlas pad is to be removably attached;
  selecting an Atlas pad whose length is equal to the measured distance between the center of the Atlas vertebra of the user and the inside surface of the Atlas bar; and
  attaching the outside end of the selected Atlas pad to the inside surface at the top of the Atlas bar.

* * * * *